United States Patent [19]
Kim

[11] Patent Number: 5,849,733
[45] Date of Patent: Dec. 15, 1998

[54] 2-THIO OR 2-OXO FLAVOPIRIDOL ANALOGS

[75] Inventor: Kyoung Soon Kim, Lawrenceville, N.J.

[73] Assignee: Bristol-Myers Squibb Co., Princeton, N.J.

[21] Appl. No.: 850,025

[22] Filed: May 1, 1997

Related U.S. Application Data

[60] Provisional application No. 60/017,529 May 10, 1996.
[51] Int. Cl.⁶ .......................... C07D 405/04; A61K 31/35
[52] U.S. Cl. .......................... 514/212; 514/320; 514/422; 540/596; 546/196; 548/525
[58] Field of Search ............................. 548/525; 546/196; 540/596; 514/422, 320, 212; 549/400

[56] References Cited

U.S. PATENT DOCUMENTS

| | | | |
|---|---|---|---|
| 4,900,727 | 2/1990 | Kattige et al. | 514/212 |
| 5,284,856 | 2/1994 | Naik et al. | 514/320 |

OTHER PUBLICATIONS

Kaur et al., Growth Inhibition with Reversible Cell Cycle Arrest of Carcinoma cells by Flavone L86–8275, J. of the National Cancer Institute, vol. 84, No. 22, pp. 1736–1740, Nov. 1992.

*Primary Examiner*—Mukund J. Shah
*Assistant Examiner*—Deepak Rao
*Attorney, Agent, or Firm*—Frank P. Hoffman

[57] ABSTRACT

Compounds of the formula I

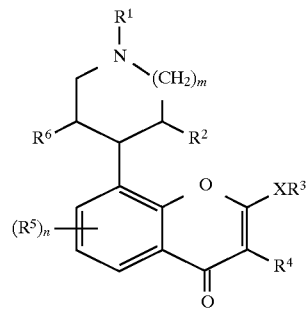

and pharmaceutically acceptable salts thereof, wherein X, $R^1$, $R^2$, $R^3$, $R^4$, $R^5$, $R^6$, m and n are as defined in the disclosure. The compounds of formula I are protein kinase inhibitors and are useful in the treatment of proliferative diseases.

19 Claims, No Drawings

2-THIO OR 2-OXO FLAVOPIRIDOL ANALOGS

This application claims priority benefit of Provisional Application No. 60/017,529 filed May 10, 1996.

BRIEF DESCRIPTION OF THE INVENTION

The present invention is directed to compounds of the formula

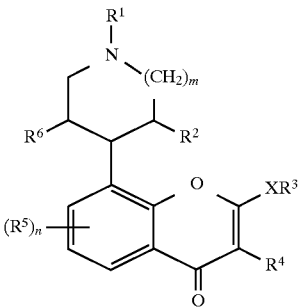

and pharmaceutically acceptable salts thereof. As used in formula I, and throughout the specification, the symbols have the following meanings:

X is oxygen or sulfur;

$R^1$ is hydrogen, alkyl, aryl, arylalkyl, cycloalkyl, —$(CH_2)_q$—$NR^7R^8$, alkylcarbonyl, arylcarbonyl, arylalkylcarbonyl, alkyloxycarbonyl, arylalkyloxycarbonyl or aryloxycarbonyl;

$R^2$ is hydrogen, alkyl, arylalkyl, aryl, cycloalkyl, hydroxy, alkoxy, arylalkoxy, aryloxy, alkylcarbonyloxy, arylalkylcarbonyloxy, arylcarbonyloxy, carboxy, alkyloxycarbonyl, arylalkoxycarbonyl, aryloxycarbonyl, amino, —$NR^7R^8$, thiol, alkylthio, arylalkylthio or arylthio;

$R^3$ is alkyl, cycloalkyl, aryl, arylalkyl, heterocycle or heterocycloalkyl;

$R^4$ is hydrogen, alkyl, aryl, arylalkyl, nitro, amino, —$(CH_2)_p$—$NR^7R^8$, halogen, hydroxy, alkoxy, carboxy, heterocycle or alkyloxycarbonyl;

$R^5$ is hydrogen, alkyl, arylalkyl, aryl, cycloalkyl, hydroxy, alkoxy, arylalkoxy, aryloxy, alkylcarbonyloxy, arylalkylcarbonyloxy, arylcarbonyloxy, carboxy, alkyloxycarbonyl, arylalkoxycarbonyl, cyano, nitro, —$NR^7R^8$, halogen, alkylhalo, —CHO, alkylS(O)$_m$— or —OC(O)$NR^7R^8$;

$R^6$ is hydrogen, alkyl, arylalkyl, aryl, cycloalkyl, hydroxy, alkoxy, arylalkoxy, aryloxy, alkylcarbonyloxy, arylalkylcarbonyloxy, arylcarbonyloxy, carboxy, alkyloxycarbonyl, arylalkoxycarbonyl, aryloxycarbonyl, amino, —$NR^7R^8$, thiol, alkylthio, arylalkylthio or arylthio;

$R^7$ and $R^8$ are independently hydrogen, alkyl, aryl, arylalkyl, cycloalkyl, heterocycle or alkylcarbonyl; or $R^7$ and $R^8$ together with the nitrogen atom to which they are bonded can form a heterocycle;

m is an integer of 0 to 2;

n is an integer of 0 to 3;

p is an integer of 1 to 3; and q is an integer of 2 to 5.

The compounds of formula I are protein kinase inhibitors and are useful in the treatment of proliferative diseases, for example, cancer, inflammation and arthritis.

DESCRIPTION OF THE INVENTION

The present invention provides for compounds of formula I, pharmaceutical compositions employing such compounds and for methods of using such compounds.

Listed below are definitions of various terms used to describe the compounds of the instant invention. These definitions apply to the terms as they are used throughout the specification (unless they are otherwise limited in specific instances) either individually or as part of a larger group.

It should be noted that any heteroatom with unsatisfied valances is assumed to have the hydrogen atom to satisfy the valances.

The term "alkyl" or "alk" refers to optionally substituted, straight and branched chain saturated hydrocarbon groups having 1 to 12 carbon atoms. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include but are not limited to one or more of the following groups: halo (such as $CCl_3$ or $CF_3$), alkoxy, alkylthio, hydroxy, carboxy (—COOH), alkyloxycarbonyl, alkylcarbonyloxy, amino (—$NH_2$), —$NR^7R^8$, carbamoyl (—NHCOO— or —OCONH—), urea (—NHCONH—) or thiol (—SH).

The terms "alkoxy" or "alkylthio", as used herein, denote an alkyl group as described above bonded through an oxygen linkage (—O—) or a sulfur linkage (—S—), respectively.

The term "alkyloxycarbonyl", as used herein, denotes an alkoxy group bonded through a carbonyl group.

The term "alkylcarbonyl" refers to an alkyl group bonded through a carbonyl group.

The term "alkylcarbonyloxy", as used herein, denotes an alkylcarbonyl group which is bonded through an oxygen linkage.

The term "cycloalkyl" refers to optionally substituted, saturated cyclic hydrocarbon ring systems, preferably containing 1 to 3 rings and 3 to 7 carbons per ring. Exemplary unsubstituted such groups include cyclopropyl, cyclobutyl, cyclopentyl, cyclohexyl, etc. Exemplary substituents include one or more of the following groups: halogen, alkyl, alkoxy, alkyl hydroxy, amino, nitro, cyano, thiol and/or alkylthio.

The term "aryl" refers to monocyclic or bicyclic aromatic groups containing from 6 to 10 carbons in the ring portion, (such as phenyl or naphthyl), and may optionally be substituted with one or more groups selected from halogen, alkyl, alkoxy, alkylS(O)$_m$—, hydroxy, carboxy, carbamoyl, alkyloxycarbonyl, —$CONR^7R^8$, nitro, trifluoromethyl, amino and —$NR^7R^8$.

The term "heterocycle" or "heterocyclo" denotes optionally substituted, fully saturated or unsaturated, aromatic or non-aromatic cyclic groups having at least one heteroatom in at least one ring, preferably monocyclic or bicyclic groups having 5 or 6 atoms in each ring. The heterocyclo group may, for example, have 1 or 2 oxygen atoms and/or 1 or 2 sulfur atoms, and/or 1 to 4 nitrogen atoms in the ring. Each heterocyclo group may be bonded through any carbon or heteroatom of the ring system. Exemplary heterocyclo groups include the following: thienyl, furyl, pyrrolyl, pyridyl, imidazolyl, pyrrolidinyl, piperidinyl, azepinyl, indolyl, isoindolyl, quinolinyl, isoquinolinyl, benzothiazolyl, benzoxazolyl, benzimidazolyl, benzoxadiazolyl, benzofurazanyl and tetrahydropyranyl. Exemplary substituents include one or more of the following: halo, alkyl, alkoxy, hydroxy, cycloalkyl, hydroxy, nitro, cyano, amino, alkylS(O)$_m$— or thiol.

The term "halogen" or "halo" refers to chlorine, bromine, fluorine or iodine.

Suitable examples of salts of the compounds according to the invention with inorganic or organic acids are hydrochloride, hydrobromide, sulfate, phosphate, acetate, oxalate, tartrate, citrate, maleate or fumarate. Salts which are unsuitable for pharmaceutical uses but which can be employed, for example, for the isolation or purification of free compounds I or their pharmaceutically acceptable salts, are also included.

All stereoisomers of the compounds of the instant invention are contemplated, either in admixture or in pure or substantially pure form. The definition of the compounds according to the invention embraces all possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization.

It should be understood that the present invention includes prodrug forms of the compounds of formula I.

The compounds of the instant invention may be in the free or hydrate form, and may be obtained by methods exemplified by the following descriptions.

Compounds of formula I where X is sulfur can be prepared by reacting compounds of formula

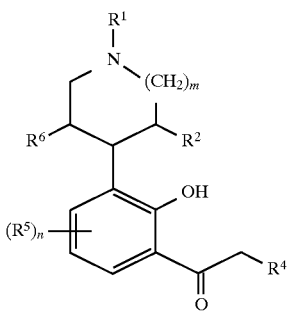
II with a sulfur containing compound such as $CS_2$ in the presence of a base such as sodium hydride, a metal alkylamide, metal alkylsilylamide, etc., followed by treatment with an acid such as a mineral acid (for example, HCl) or an organic acid (for example, $CF_3CO_2H$ or $CH_3SO_3H$) to obtain compounds of formula

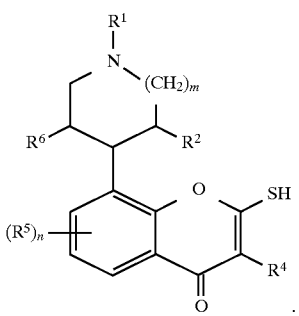
III

Compounds of formula III are then reacted with a compound of formula

R³L      IV where R³ is as defined previously and L is a leaving group such as halogen or mesylate in the presence of a base such as alkalimetal carbonate, sodium hydride, etc. to provide the compounds of formula I where X is sulfur. Alternatively, L may be a group that can react with the sulfur such as an epoxide, an α, β unsaturated ketone, ester or aldehyde, and the like.

Compounds of formula I where X is oxygen may be prepared from compounds of formula I where X is sulfur and R³ is alkyl, by reaction with an oxidizing agent such as m-chloroperbenzoic acid or $NaBO_3$ in an acidic medium such as HOAc or trifluoroacetic acid to provide compounds of formula

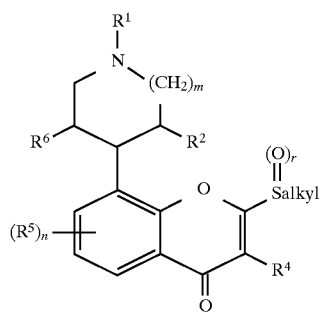
V where r is 1 or 2. Compounds of formula V are then reacted with a compound of formula

R³OH      VI in the presence of a base such as a metal carbonate, potassium t-butoxide or sodium hydride to form compounds of formula I where X is oxygen.

Compounds of formula I where X is sulfur can also be prepared from compounds of formula I where XR³ is S-alkyl, or from compounds of formula V by reaction with a compound of formula

R³SH      VII in the presence of a base such as a metal carbonate, potassium t-butoxide or sodium hydride.

Compounds of formula I where R⁵ is hydroxy can also be prepared from compounds of formula I where R⁵ is alkoxy by treatment with an acid such as pyridinium hydrochloride or a Lewis acid such as $BBr_3$.

Compounds of formula II, where R⁴ is hydrogen are known compounds and may be prepared by processes disclosed in U.S. Pat. No. 4,900,727, issued Feb. 13, 1990, which is incorporated by reference herein. An exemplary method for preparing compounds of formula II, where R⁴ is hydrogen is shown in the following reaction scheme:

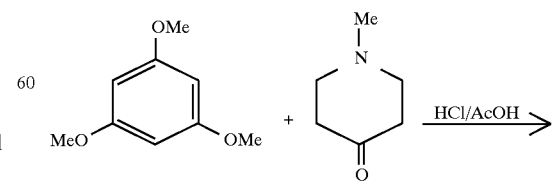

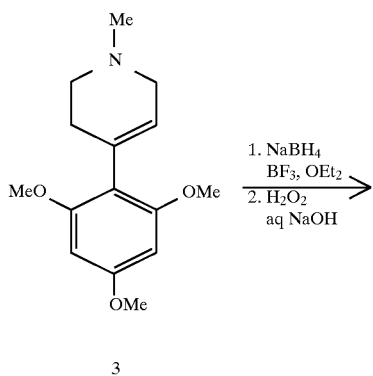

3

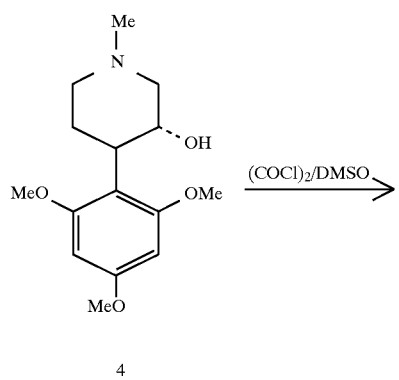

4

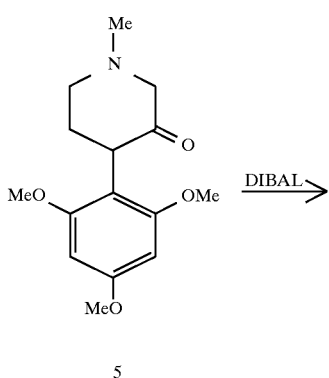

5

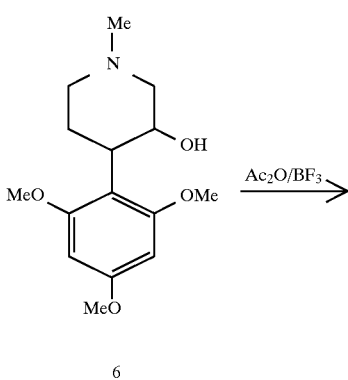

6

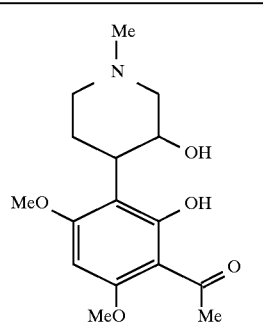

7

Compounds of formula 7 in the above scheme are compounds of formula II. Compounds of formula II where $R^4$ is other than hydrogen can be prepared by similar methods.

Intermediates of this invention may also be prepared by processes disclosed in U.S. Pat. No. 5,284,856, or by modification of procedures described in U.S. Pat. No. 5,284,856, which is incorporated by reference herein.

Compounds of formula IV, VI and VII are commercially available or may be prepared by methods known to one of ordinary skill in the art.

All other compounds of formula I may be prepared by modification of the procedures described herein.

The preferred compounds of formula I are those where:

$R^1$ is alkyl;
$R^2$ is hydroxy;
$R^3$ is alkyl, aryl, heterocyclo or arylalkyl;
$R^4$ is hydrogen or alkyl;
$R^5$ is hydroxy or alkoxy;
$R^6$ is hydrogen;
m is the integer 1; and
n is the integer 2.

The most preferred compounds of formula I are those where:

$R^1$ is alkyl;
$R^2$ is hydroxy;
$R^3$ is aryl or arylalkyl;
$R^4$ is hydrogen;
$R^5$ is hydroxy;
$R^6$ is hydrogen;
m is the integer 1; and
n is the integer 2.

The compounds according to the invention have pharmacological properties; in particular, the compounds of formula I are inhibitors of protein kinases such as the cyclin dependent kinases (cdks), for example, cdc2 (cdk1), cdk2, and cdk4. The compounds of formula I are therefore expected to be useful in the therapy of proliferative diseases such as cancer, inflammation, and arthritis (Jorg Czech et al., "Antitumoral Activity of Flavone L 86-8275", *International Journal of Oncology* 6, 31–36 (1995); Gurmeet Kaur et al., "Growth Inhibition With Reversible Cell Cycle Arrest of Carcinoma Cells by Flavone L86-8275", *Journal of the National Cancer Institute*, 84, No. 22, 1736–1740 (1992); which are incorporated by reference herein).

More specifically, the compounds of formula I are useful in the treatment of a variety of cancers, including (but not limited to) the following:

carcinoma, including that of the bladder, breast, colon, kidney, liver, lung, ovary, pancreas, stomach, cervix, thyroid, prostate, and skin;

hematopoietic tumors of lymphoid lineage, including acute lymphocytic leukemia, B-cell lymphoma, and Burkett's lymphoma;

hematopoietic tumors of myeloid lineage, including acute and chronic myelogenous leukemias and promyelocytic leukemia;

tumors of mesenchymal origin, including fibrosarcoma and rhabdomyosarcoma; and other tumors, including melanoma, seminoma, teratocarcinoma, osteosarcoma, neuroblastoma and glioma.

Due to the key role of cdks in the regulation of cellular proliferation in general, inhibitors could act as reversible cytostatic agents which may be useful in the treatment of any disease process which features abnormal cellular proliferation, e.g., neuro-fibromatosis, atherosclerosis, pulmonary fibrosis, arthritis, psoriasis, glomerulonephritis, restenosis following angioplasty or vascular surgery, hypertrophic scar formation, and endotoxic shock.

Compounds of formula I may also be useful in the treatment of Alzheimer's disease, as suggested by the recent finding that cdk5 is involved in the phosphorylation of tau protein (*J. Biochem*, 117, 741–749 (1995)).

Compounds of formula I may also act as inhibitors of other protein kinases, e.g., protein kinase C, her2, raf1, MEK1, MAP kinase, EGF receptor, PDGF receptor, IGF receptor, PI3 kinase, wee1 kinase, Src, Ab1 and thus be effective in the treatment of diseases associated with other protein kinases.

The compounds of this invention may also be useful in combination with known anti-cancer, cytostatic, and cytotoxic agents. If formulated as a fixed dose, such combination products employ the compounds of this invention within the dosage range described below and the other pharmaceutically active agent within its approved dosage range. For example, the cdc2 inhibitor olomucine has been found to act synergistically with known cytotoxic agents in inducing apoptosis (*J. Cell Sci.*, 108, 2897 (1995)). Compounds of formula I may be used sequentially with known anticancer or cytotoxic agents when a combination formulation is inappropriate.

The pharmacological properties of the compounds of this invention may be confirmed by a number of pharmacological assays. The exemplified pharmacological assays which follow have been carried out with the compounds according to the invention and their salts. The compounds of examples 1 to 26 exhibited cdc2/cyclin B1 kinase activity with $IC_{50}$ values less than 10 μM. The compounds of examples 1 to 26 exhibited cdk2/cyclin E kinase activity with $IC_{50}$ values less than 20 μM. The compounds of examples 1 to 27 exhibited cdk4/cyclin D1 kinase activity with $IC_{50}$ values less than 100 μM.

cdc2/cyclin B1 Kinase Assay cdc2/cyclin B1 kinase activity was determined by monitoring the incorporation of $^{32}P$ into histone HI. The reaction consisted of 50 ng baculovirus expressed GST-cdc2, 75 ng baculovirus expressed GST-cyclin B1, 1 μg histone HI (Boehringer Mannheim), 0.2 μCi of $^{32}P$ γ-ATP and 25 μM ATP in kinase buffer (50 mM Tris, pH 8.0, 10 mM $MgCl_2$, 1 mM EGTA, 0.5 mM DTT). The reaction was incubated at 30° C. for 30 minutes and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter (Marshak, D. R., Vanderberg, M. T., Bae, Y. S., Yu, I. J., *J. of Cellular Biochemistry*, 45, 391–400 (1991), incorporated by reference herein).

cdk2/cyclin E Kinase Assay cdk2/cyclin E kinase activity was determined by monitoring the incorporation of $^{32}P$ into the retinoblastoma protein. The reaction consisted of 2.5 ng baculovirus expressed GST-cdk2/cyclin E, 500 ng bacterially produced GST-retinoblastoma protein (aa 776–928), 0.2 μCi $^{32}P$ γ-ATP and 25 μM ATP in kinase buffer (50 mM Hepes, pH 8.0, 10 mM $MgCl_2$, 5 mM EGTA, 2 mM DTT). The reaction was incubated at 30° C. for 30 minutes and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter.

cdk4/cyclin D1 Kinase Assay cdk4/cyclin D1 kinase activity was determined by monitoring the incorporation of $^{32}P$ into the retinoblastoma protein. The reaction consisted of 165 ng baculovirus expressed GST-cdk4, 282 ng bacterially expressed S-tag cyclin D1, 500 ng bacterially produced GST-retinoblastoma protein (aa 776–928), 0.2 μCi $^{32}P$ γ-ATP and 25 μM ATP in kinase buffer (50 mM Hepes, pH 8.0, 10 mM $MgCl_2$, 5 mM EGTA, 2 mM DTT). The reaction was incubated at 30° C. for 1 hour and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter (Matsushime, H., Ewen, M. E., Strom, D. K., Kato, J-Y., Hanks, S. K., Roussel, M. F., Sherr, C. J. (1992) *Cell*, 71, 323–334, incorporated by reference herein).

Further subject matter of the invention also includes pharmaceuticals for use as described above including controlling cancer, inflammation and arthritis, which contain at least one compound of the formula I as defined above or at least one of its pharmacologically acceptable acid addition salts, and the use of a compound of the formula I as defined above for the preparation of a pharmaceutical having activity against proliferative diseases as described previously including against cancer, inflammation and/or arthritis.

The compounds of formula I can be formulated for use in compositions such as tablets, capsules or elixirs for oral administration, in sterile solutions or suspensions for parenteral or intranasal administration, or in transdermal patches. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I are used according to the invention in the generally known fashion which is known to one of ordinary skill in the art. For pharmaceuticals, an effective amount of the active substance mentioned is employed either per se or preferably in combination with suitable pharmaceutical auxiliaries in the form of tablets, coated tablets, capsules, suppositories, emulsions, suspensions or solutions, the active compound content being up to about 95%, preferably between 10 and 75%.

Besides auxiliaries for tablets, or solvents, gel formers, bases for suppositories, and other excipients for the active substance, it is possible to use, for example, antioxidants, dispersants, emulsifiers, defoamers, flavor corrigants, preservatives, solubilizers or colorants.

The active substance can be administered orally, subcutaneously, sublingually, transdermally, intravenously or in the form of vaginal or rectal suppositories, intravenous and oral administration being preferred. For a form of oral administration, the active substance may be mixed with other compounds together with the additives which are suitable for this purpose, such as excipients, stabilizers or inert diluents, and customary methods can be used for bringing it into suitable administration forms, such as tablets, coated tablets, hard-gelatin capsules, and aqueous alcoholic or oily suspensions or solutions. Examples of inert excipients which can be used are gum arabic, magnesia, lactose, glucose or starch, in particular corn starch. In this context, the formulation can be prepared as dry granules or moist granules. Examples of suitable oily excipients or solvents are vegetable or animal oils, such as sunflower oil or codliver oil.

For subcutaneous or intravenous administration, a solution, suspension or emulsion of the active substance is formed, if appropriate using substances which are conventional for this purpose, such as solubilizers, emulsifiers or other auxiliaries. Examples of suitable solvents are water, physiological sodium chloride solution or alcohols, for example, ethanol, propanol or glycerol, and also sugar solutions, such as glucose solutions or mannitol solutions, or a mixture of the various solvents which have been mentioned.

The dose of the compounds of this invention which is to be administered can cover a wide range. The dose to be administered daily is to be selected to suit the desired effect. About 20 to 1,000 mg are preferably administered daily per patient. If required, higher or lower daily doses can also be administered.

The following examples and preparations describe the manner and process of making and using the invention and are illustrative rather than limiting. It should be understood that there may be other embodiments which fall within the spirit and scope of the invention as defined by the claims appended hereto. In the following examples where preparative HPLC has been utilized, solvent A refers to $H_2O:MeOH:TFA$; 90:10:0.1 by volume and solvent B refers to $H_2O:MeOH:TFA$; 10:90:0.1 by volume.

EXAMPLE 1 cis-(±)-2-(Ethylthio)-5,7-dihydroxy-8-(3-hydroxy-1-methyl-4-piperidinyl)-4H-1-henzopyran-4-one

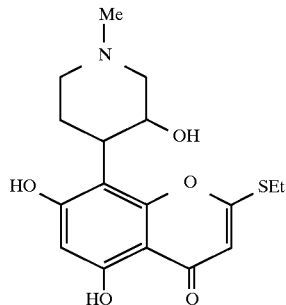

A. trans-(±)-1-Methyl-4-(2,4,6-trimethoxy-phenyl)-3-piperidinol 1. 1,2,5,6-Tetrahydro-1-methyl-4-(2,4,6-tri-methoxyphenyl) pyridine To a solution of trimethoxybenzene (16.8 g, 0.1 mol) in acetic acid (40 mL) at room temperature was added N-methyl-4-piperidone (13.6 g, 0.12 mol), followed by introducing gaseous HCl to saturation. The resulting mixture was stirred between 95°–100° C. for 3 hours. It was concentrated in vacuo and the residue was diluted with water (150 mL). It was extracted with ethyl ether (2×50 mL) and the aqueous solution was made alkaline with concentrated NaOH solution. The solid was collected, washed with water and dried to afford the title compound (21.2 g, 81%) as a solid, mp 118°–122° C.

2. trans-(±)-1-Methyl-4-(2,4,6-trimethoxyphenyl)-3-piperidinol

To a mixture of the title 1 compound (10 g, 38 mmol) and $NaBH_4$ (6 g, 0.16 mol) in diglyme (70 mL) at 20° C. was added dropwise a solution of $BF_3$ etherate (21 mL) in diglyme (20 mL) over 1 hour. The resulting mixture was stirred at 50° C. for 1 hour and cooled to 0° C. Water (10 mL) was added dropwise, followed by concentrated HCl solution (60 mL). The mixture was stirred at 50°–60° C. for 2 hours. It was cooled to 0° C. and made alkaline with 50% NaOH solution. Hydrogen peroxide (30%, 10 mL) was added and the mixture stirred at 50°–60° C. for 2 hours. The reaction mixture was cooled to room temperature and extracted with ethyl acetate (3×20 mL). The ethyl acetate extract was concentrated and 2N HCl solution (20 mL) was added. It was extracted with ethyl acetate (2×20 mL) and the aqueous layer was rendered alkaline with 2N NaOH solution. It was extracted with ethyl ether (4×20 mL). The ether extract was washed with brine, dried ($Na_2SO_4$), and concentrated. The residue was chromatographed on $SiO_2$ eluting with ethyl acetate:methanol:triethylamine (100:10:5) to furnish the title compound (6.5 g, 61%) as a foam.

B. (±)-1-Methyl-4(2,4,6-trimethoxyphenyl)-3-piperidinone

To a solution of oxalyl chloride (8 mL, 91.7 mmol) in $CH_2Cl_2$ (200 mL) at −78° C. was added DMSO (14 mL, 197.4 mmol) with stirring. The resulting mixture was stirred for 5 minutes and a solution of the title A compound (24.8 g, 88.26 mmol) in $CH_2Cl_2$ (120 mL) was added dropwise. After the completion of addition the mixture was stirred at −78° C. for 30 minutes. $Et_3N$ (62 mL, 444 mmol) was added and the mixture was warmed up to −30° C. Aqueous sodium carbonate solution (200 mL, 10%) was added and the $CH_2Cl_2$ layer was taken. The aqueous layer was extracted with $CH_2Cl_2$ (3×100 mL). The combined organic solution was washed with brine, dried over $Na_2SO_4$ and concentrated to afford a solid. The solid was recrystallized from isopropanol or purified by column chromatography (SiO$_2$, EtOAc:MeOH:Et$_3$N; 100:10:2) to afford the title compound as a solid, 16.8 g (68%), mp 112° C.

C. cis-(±)-1-Methyl-4-(2,4,6-trimethoxyphenyl)-3-piperidinol

To a solution of the title B compound (9.8 g, 35.1 mmol) in toluene (100 mL) at −70° C. was added DIBAL (40 mL of 1.5M solution in toluene) at such a rate that kept the reaction temperature below −60° C. After the addition, it was stirred at −65° C. for 2 hours and quenched by MeOH (20 mL) below −60° C. After quenching, NaOH solution (2N, 100 mL) was added. The toluene solution was taken and the aqueous layer was extracted with CH$_2$Cl$_2$ (3×100 mL). The combined solution was washed with brine, dried over Na$_2$SO$_4$, filtered and concentrated to give the crude product, which was crystallized from acetone to afford the title compound as a solid, 7.20 g (73%), mp 124° C. (containing about 5 to 8% trans isomer).

D. cis-(±)-4-(3-Acetyl-2-hydroxy-4,6-dimethoxyphenyl)-1-methyl-3-piperidinol

To a solution of the title C compound (6.0 g, 21.4 mmol) in CH$_2$Cl$_2$ (80 mL) was added BF$_3$ etherate solution (18 mL), followed by acetic anhydride (15 mL). The mixture was stirred at room temperature for 16 hours and concentrated to remove the CH$_2$Cl$_2$. The residue was cooled to 0° C. and MeOH (100 mL) was added dropwise. It was concentrated again and the residue was stirred with aqueous KOH solution (100 mL, 20%) and MeOH (100 mL) at 50° C. for 5 hours. The mixture was concentrated and adjusted to pH 10 with 2N HCl solution. The product was extracted with CH$_2$Cl$_2$ (3×50 mL). The CH$_2$Cl$_2$ extract was dried over Na$_2$SO$_4$ and concentrated to afford the crude product, which was purified by column chromatography (SiO$_2$, EtOAc:MeOH:Et$_3$N; 100:10:2) to give the title compound as a solid, 6.1 g (92%), mp 216° C.

E. cis-(±)-8-(3-Hydroxy-1-methyl-4piperidinyl)-2-mercapto-5,7-dimethoxy-4-H-1-benzopyran-4-one To a mixture of the title D compound (2.05 g, 6.6 mmol) in THF (10 mL) and CS$_2$ (3 mL) at −60° C. under argon was added LiN(SiMe$_3$)$_2$ solution (50 mL of 1M solution in THF). The coolant was removed and it was stirred at room temperature for 2 hours (monitored by HPLC). To this mixture was then added sulfuric acid (2.5 N or 10%) to pH 1. It was stirred at room temperature for 2 hours. It was concentrated to remove the excess CS$_2$ and THF. To the residue was added MeOH (50 mL) and the resulting mixture was filtered to remove the solid. The filtrate was concentrated and purified by preparative HPLC (YMC OD S-10 50×500 mm, flow rate 84 mL/minute; UV 254 nm; solvents 35% B). The desired fractions were pooled and concentrated. The residue was lyophilized to afford the title compound as a yellow solid, 1.98 g (64%), mp 184°–185° C.

F. cis-(±)-2-(Ethylthio)-8-(3-hydroxy-1-methyl-4-piperidinyl)-5,7-dimethoxy-4H-1-benzopyran-4-one A mixture of the title E compound (1.08 g, 2.32 mmol) and Cs$_2$CO$_3$ (1.51 g, 4.64 mmol) in DMF (10 mL) was stirred at room temperature under argon for 15 minutes. It was cooled to −20° C. and EtI (362 mg, 2.32 mmol) was added. The coolant was removed and it was stirred at room temperature for 1 hour. Water (50 mL) was then added and it was extracted with CH$_2$Cl$_2$ (3×20 mL). The CH$_2$Cl$_2$ extract was dried over Na$_2$SO$_4$ and concentrated. The residue was purified by column chromatography (SiO$_2$, EtOAc:MeOH:Et$_3$N; 100:10:2) to afford the title compound (660 mg, 79%) as a solid, mp 170° C.

Alternatively, the title F compound may be prepared as follows:

To a suspension of the title D compound (cis-(±)-4-(3-acetyl-2-hydroxy-4,6-dimethoxyphenyl)-1-methyl-3-piperidinol; 309 mg, 1 mmol) in THF (4 mL) and carbon disulfide (0.3 mL, 5 mmol) at room temperature was added a solution of lithium hexamethylsilylamide (6 mL of 1M in THF, 6 mmol) slowly. The mixture was stirred at room temperature for 2 hours and the reaction was quenched by adding water (2 mL). The mixture was concentrated to remove the excess CS$_2$ and THF. To the residue was added MeOH (3 mL) followed by TFA-H$_2$O (1:1, 1.6 mL). The resulting mixture was stirred at room temperature for 1 hour and concentrated to remove most of the solvents. To this residue was add DMF (5 mL) followed by cesium carbonate (1.63 g, 5 mmol). It was flushed with argon, stirred at 0° C. for 20 minutes and ethyl iodide (80 μL, 1.1 mmol) was added. The mixture was stirred overnight at room temperature. It was diluted with water (20 mL) and extracted with CH$_2$Cl$_2$ (3×20 mL). The CH$_2$Cl$_2$ extract was washed with water and concentrated. The residue was purified by flash chromatography column chromatography (SiO$_2$, EtOAc:MeOH:Et$_3$N 100:15:2) to afford the title F compound (205 mg, 54%) as a foam.

G. cis-(±)-2-(Ethylthio)-5,7-dihydroxy-8-(3-hydroxy-1-methyl-4-piperidinyl)-4H-1-benzopyran-4-one To a solution of the title F compound (144 mg, 0.4 mmol) in 1,2-dichloroethane (2 mL) at room temperature was added a solution of BBr$_3$ (0.3 mL of neat BBr$_3$, 3.2 mmol). The resulting mixture was stirred at 80° C. for 5 hours. It was cooled to 0° C., quenched by MeOH (5 mL) and neutralized with aqueous NaHCO$_3$ solution. It was concentrated and the residue was purified by preparative HPLC (YMC OD S-10 30×500 mm; 40% B; flow rate 49 mL/minute; UV 254 nm). Those containing the desired compound were pooled, concentrated and lyophilized to afford the title compounds a solid(121 mg, 67%), mp 105° C.

$^1$H NMR (CD$_3$OD) δ6.39 (s, 1H), 6.25 (s, 1H), 4.39 (m, 1H), 3.92 (m, 1H), 3.73–3.25 (m, 8H), 3.04 (s, 3H), 1.98 (m, 1H), 1.55 (t, J=7.0 Hz, 3H) ppm;

$^{13}$C NMR (CD$_3$OD) δ181.9, 171.6, 163.9, 162.1, 158.0, 106.7, 105.1, 101.1, 67.9, 61.7, 56.7, 44.2, 37.3, 26.6, 23.3, 14.3 ppm; MS (ESI.) m/e 350 (M−H)$^-$.

Anal Calc'd for C$_{17}$H$_{21}$NO$_5$S.1.00 H$_2$O.1.10 C$_2$HF$_3$O$_2$: C, 46.60; H, 4.91; N, 2.83; Found: C, 46.72; H, 4.55; N, 2.79.

EXAMPLE 2 cis-(±)-5,7-Dihydroxy-8-(3-hydroxy-1-methyl-4-piperidinyl)-2-(phenylthio)-4H-1-benzopyran-4-one

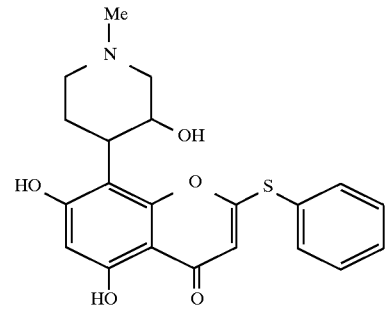

A mixture of the title compound of Example 1 (cis-(±)-2-(ethylthio)-5,7-dihydroxy-8-(3-hydroxy-1-methyl-4-piperidinyl)-4H-1-benzopyran-4-one: 50 mg, 0.10 mmol), thiophenol (110 mg, 1 mmol) and NaHCO$_3$ (100 mg) in DMF (0.5 mL) was stirred at 100° C. for 2 hours. The mixture was cooled to room temperature, filtered and purified directly by preparative HPLC (YMC OD S-10 30×500 mm; 60% B; flow rate 49 mL/minute; UV 254 nm). Those fractions containing the desired compound were pooled, concentrated and lyophilized to afford the title compound (21 mg, 35%) as a solid, mp 82° C. (softened).

$^1$H NMR (CD$_3$OD) δ7.73 (m, 2H), 7.62 (m, 3H), 6.25 (s, 1H), 5.86 (s, 1H), 4.08 (m, 1H), 3.52–2.93 (m, 6H), 2.88 (s, 3H), 1.68 (m, 1H) ppm;

$^{13}$C NMR (CD$_3$OD) δ182.1, 171.0, 164.1, 162.1, 157.9, 136.6, 132.0, 131.5, 128.0, 107.7, 106.7, 105.2, 101.3, 67.8, 61.7, 56.7, 44.3, 37.1, 23.1 ppm; MS (ESI.) m/e 400 (M+H)$^+$.

Anal Calc'd for C$_{21}$H$_{21}$NO$_5$S.0.50 H$_2$O.1.60 C$_2$HF$_3$O$_2$: C, 49.19; H, 4.03; N, 2.37; Found: C, 49.21; H, 4.00; N, 2.39.

EXAMPLE 3 cis-(±)-2-(Butylthio)-5,7-dihydroxy-8-(3-hydroxy-1-methyl-4-piperidinyl)-4H-1-benzopyran-4-one

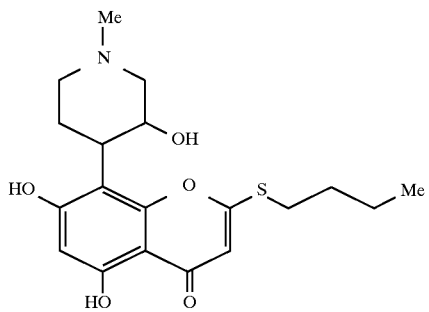

A. cis-(±)-2-(Butylthio)-8-(3-hydroxy-1-methyl-4-piperidinyl)-5,7-dimethoxy-4H-1-benzopyran-4-one A mixture of the title E compound of Example 1 (cis-(±)-8-(3-hydroxy-1-methyl-4-piperidinyl)-2-mercapto-5,7-dimethoxy-4H-1-benzopyran-4-one; 116 mg, 0.25 mmol) and Cs$_2$CO$_3$ (244 mg, 0.75 mmol) in DMF (1 mL) was stirred at room temperature under argon for 15 minutes. It was cooled to −20° C. and iodobutane (46 mg, 0.25 mmol) was added. The coolant was removed and it was stirred at room temperature for 1 hour. The mixture was directly purified by column chromatography (SiO$_2$, EtOAc:MeOH:Et$_3$N; 100:10:2) to afford the title compound as a foam, 79 mg (77%).

B. cis-(±)-5,7-Dihydroxy-8-(3-hydroxy-1-methyl-4-piperidinyl)-2-(phenylthio)-4-1-benzopyran-4-one A suspension of the title A compound (78 mg, 0.192 mmol) in 1,2-dichloroethane (1.0 mL) and BBr$_3$ (1.0 mL of 2M solution in ClCH$_2$CH$_2$Cl, 2.0 mmol) was stirred at 100° C. for 4 hours. It was cooled to 0° C. and quenched by MeOH (5 mL). It was neutralized with NaHCO$_3$ solution and purified by preparative HPLC (YMC OD S-10 30×500 mm; 60% B; flow rate 49 mL/minute; UV 254 nm). Those fractions containing the desired compound were pooled, concentrated and lyophilized to afford the title compound as a solid (24 mg, 21%), mp 96° C. (softened).

$^1$H NMR (CD$_3$OD) δ6.28 (s, 1H), 6.16 (s, 1H), 4.22 (m, 1H), 3.60–3.11 (m, 8H), 2.89 (s, 3H), 1.85 (m, 1H), 1.75 (m, 2H), 1.56 (m, 2H), 0.98 (t, J=7.6 Hz, 3H) ppm;

$^{13}$C NMR (CD$_3$OD) δ182.1, 172.2, 163.9, 162.3, 158.3, 106.8, 106.6, 105.2, 100.9, 68.0, 61.9, 56.9, 44.3, 37.6, 32.1, 31.8, 23.4, 22.9, 13.9 ppm; MS (ESI.) m/e 380 (M+H)$^+$.

Anal Calc'd for C$_{19}$H$_{25}$NO$_5$S.0.50 H$_2$O.1.70 C$_2$HF$_3$O$_2$: C, 46.20; H, 4.79; N, 2.41; Found: C, 46.17; H, 4.89; N, 2.40.

EXAMPLE 4 cis-(±)-2-(Ethylthio)-5-hydroxy-8-(3-hydroxy-1-methyl-4-piperidinyl)-7-methoxy-4H-1-benzopyran-4-one

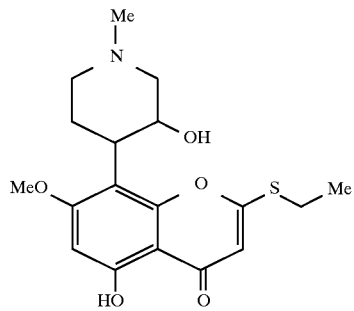

A mixture of the title F compound of Example 1 (cis-(±)-2-(ethylthio)-8-(3-hydroxy-1-methyl-4-piperidinyl)-5,7-dimethoxy-4H-1-benzopyran-4-one: 36.1 mg, 0.1 mmol) and BCl$_3$ (0.4 mL of 1M in CH$_2$Cl$_2$, 0.4 mmol) was stirred at −20° C. for 0.5 hour and at room temperature for 1 hour. It was cooled to 0° C. and quenched by water (5 mL). It was made alkaline with Na$_2$CO$_3$ solution and extracted with CH$_2$Cl$_2$ (3×5 mL). The CH$_2$Cl$_2$ extract was dried over Na$_2$SO$_4$ and concentrated. The residue was purified by preparative HPLC (YMC OD S-10 30×500 mm; 40% B; flow rate 49 mL/minute; UV 254 nm). Those containing the desired compound were pooled, concentrated and lyophilized to afford the title compound as a solid (46 mg, 91%), mp 60° C. (softened).

$^1$H NMR (CD$_3$OD) δ6.44 (s, 1H), 6.11 (s, 1H), 4.08 (m, 1H), 3.90 (s, 3H), 3.61–3.10 (m, 8H), 2.89 (s, 3H), 1.92 (m, 1H), 1.41 (t, J=7.6 Hz, 3H) ppm;

$^{13}$C NMR (CD$_3$OD) δ182.8, 173.0, 169.1, 165.7, 163.5, 158.7, 108.5, 107.4, 106.1, 97.6, 68.4, 62.7, 57.8, 57.7, 45.1, 39.0, 27.5, 24.4, 15.0 ppm. MS (ESI.) m/e 366 (M+H)$^+$.

Anal Calc'd for C$_{18}$H$_{23}$NO$_5$S.0.60 H$_2$O.1.10 C$_2$HF$_3$O$_2$: C, 48.36; H, 5.08; N, 2.79; Found: C, 48.29; H, 5.27; N, 2.76.

EXAMPLE 5 cis-(±)-3-[[5,7-Dihydroxy-8-(3-hydroxy-1-methyl-4-piperidinyl)-4-oxo-4H-1-benzopyran-2-yl]thio] propanoic acid, methyl ester

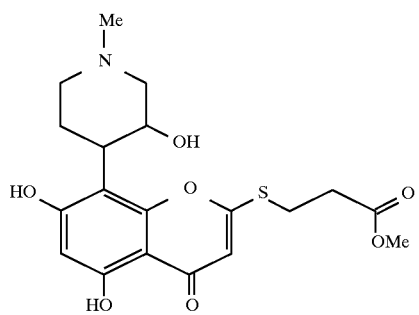

A. cis-(±)-3-[[8-(3-Hydroxy-1-methyl-4-piperidinyl)-5,7-dimethoxy-4-oxo-4H-1-benzopyran-2-yl]thio]-propanoic acid, methyl ester A mixture of the title E compound of Example 1 (cis-(±)-8-(3-hydroxy-1-methyl-4-piperidinyl)-2-mercapto-5,7-dimethoxy-4H-1-benzopyran-4-one: 232.5 mg, 0.5 mmol) and methyl acrylate (0.2 mL) in DMF (3 mL) was stirred with triethylamine (100 mg, 1 mmol) at 60°–70° C. under argon atmosphere for 2 days. It was cooled to room temperature and diluted with CH$_2$Cl$_2$ (20 mL). The solution was washed with water (20 mL), dried over Na$_2$SO$_4$ and concentrated. The residue was purified by column chromatography (SiO$_2$, EtOAc:MeOH:Et$_3$N; 100:15:2) to afford the title compound (110 mg, 52%) as a foam.

B. cis-(±)-3-[[5,7-Dihydroxy-8-(3-hydroxy-1-methyl-4-piperidinyl)-4-oxo-4H-1-benzopyran-2-yl]thio]-propanoic acid, methyl ester To a solution of the title A compound (75 mg, 0.18 mmol) in 1,2-dichloroethane (1 mL) at room temperature was added a solution of BBr$_3$ (1 mL of 2M, 2 mmol). The resulting mixture was stirred at 80° C. for 5 hours. It was cooled to 0° C., quenched by MeOH (5 mL) and neutralized with NaHCO$_3$ solution. It was concentrated and the residue was purified by preparative HPLC (YMC OD S-10 30×500 mm; 30% B; flow rate 49 mL/minute; UV 254 nm). The desired product containing fractions were pooled, concentrated and lyophilized to afford the title compound (18 mg, 17%) as a solid, mp 78° C. (softened).

$^1$H NMR (CD$_3$OD) δ6.28 (s, 1H), 6.23 (s, 1H), 4.27 (m, 1H), 3.71 (s, 3H), 3.66–3.20 (m, 1H) ppm;

$^{13}$C NMR (CD$_3$OD) δ182.5, 174.0, 170.0, 164.5, 162.7, 158.5, 108.4, 107.3, 105.7, 101.6, 68.4, 62.2, 57.1, 53.0, 44.7, 37.7, 35.0, 27.6, 23.7 ppm; MS (ESI.) m/e 410 (M+H)$^+$.

Anal Calc'd for C$_{19}$H$_{23}$NO$_7$S.0.8 H$_2$O.1.30 C$_2$HF$_3$O$_2$: C, 44.35; H, 4.56; N, 2.45; Found: C, 45.24; H, 4.42; N, 2.46.

EXAMPLE 6 cis-(±)-2-[(2-Chlorophenyl)thio]-5,7-dihydroxy-8-(3-hydroxy-1-methyl-4-piperidinyl)-4H-1-benzopyran-4-one

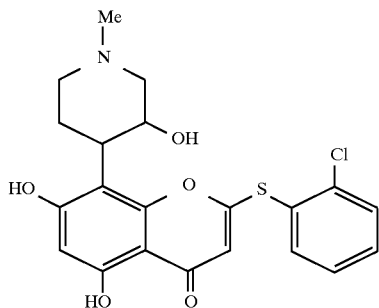

A mixture of the title compound of Example 1 (cis-(±)-2-(ethylthio)-5,7-dihydroxy-8-(3-hydroxy-1-methyl-4-piperidinyl)-4H-1-benzopyran-4-one: 46.5 mg, 0.10 mmol), 2-chlorothiophenol (144.6 mmpl, 1 mmol) and NaHCO$_3$ (100 mg, 1.19 mmol) in DMF (0.2 mL) was stirred at 90° C. for 4 hours. The mixture was cooled to room temperature and neutralized with trifluoroacetic acid (0.2 mL). The mixture was purified directly by preparative HPLC (YMC OD S-10 30×500 mm; 60% B; flow rate 49 mL/minute; UV 254 nm). Those fractions containing the desired compound were pooled, concentrated and lyophilized to afford the title compound (30 mg, 62%) as a solid, mp 226°–227° C.

$^1$H NMR (CD$_3$OD) δ7.87–7.50 (m, 4H), 6.27 (s, 1H), 5.92 (s, 1H), 4.07 (m, 1H), 3.50–2.91 (m, 7H), 2.87 (s, 3H), 1.70 (m, 1H) ppm;

$^{13}$C NMR (CD$_3$OD) δ182.6, 169.1, 164.6, 162.7, 158.4, 140.7, 139.2, 134.3, 132.7, 130.3, 127.9, 108.7, 107.2, 105.7, 101.8, 68.2, 62.2, 57.2, 44.7, 37.7, 23.5 ppm; MS (ESI.) (95100262) m/e 434 (M+H)$^+$.

Anal Calc'd for C$_{21}$H$_{20}$NO$_5$.0.6 H$_2$O.1.6 C$_2$HF$_3$O$_2$: C, 46.35; H, 3.66; N, 2.23; Found: C, 46.24; H, 3.58; N, 2.16.

EXAMPLE 7 cis-(±)-5,7-Dihydroxy-8-(3-hydroxy-1-methyl-4-piperidinyl)-2-phenoxy-4H-1-benzopyran-4-one

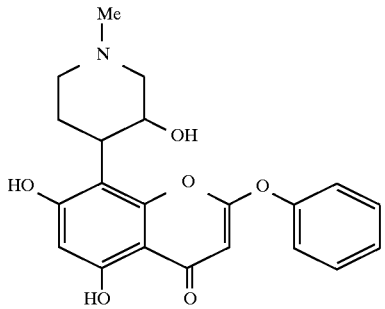

A. 2-(Ethylsulfinyl)-8-(3-hydroxy-1-methyl-4-piperidinyl)-5,7-dimethoxy-4H-1-benzopyran-4-one A solution of the title compound of Example 1 (cis-(±)-2-(ethylthio)-5,7-dihydroxy-8-(3-hydroxy-1-methyl-4-piperidinyl)-4H-1-benzopyran-4-one: 180.5 mg, 0.476 mmol) and NaBO$_3$.4 H$_2$O (153 mg, 1 mmol) in acetic acid (2 mL) was stirred at room temperature overnight. To this solution was added sodium bisulfite (100 mg) and the mixture was stirred at room temperature for 10 minutes. It was diluted with water (10 mL) and made alkaline with Na$_2$CO$_3$. The product was extracted with CH$_2$Cl$_2$ (3×10 mL) and the CH$_2$Cl$_2$ extract was dried (Na$_2$SO$_4$), concentrated to afford a diastereomeric mixture of the title compound (105 mg, 53%) as a foam.

B. cis-(±)-8-(3-Hydroxy-1-methyl-4-piperidinyl)-5,7-dimethoxy-2-phenoxy-4H-1-benzopyran-4-one A mixture of phenol (100 mg, 1.06 mmol) and NaH (40 mg, 60% in oil, 1 mmol) in THF (1 mL) was stirred at room temperature for 30 minutes and the title A compound (60 mg, 0.15 mmol) was added as a solid. The resulting mixture was stirred for 1 hour and concentrated. The residue was taken up in CH$_2$Cl$_2$ (20 mL), washed with water (10 mL) and dried (Na$_2$SO$_4$). It was concentrated and purified by flash column chromatography (SiO$_2$, EtOAc:MeOH:Et$_3$N; 100:15:2) to afford the title compound (30 mg, 49%) as a solid, mp 238°–239° C.

C. cis-(±)-5,7-Dihydroxy-8-(3-hydroxy-1-methyl-4-piperidinyl)-2-phenoxy-4H-1-benzopyran-4-one To a solution of the title B compound (25 mg, 0.061 mmol) in 1,2-dichloroethane (2 mL) at room temperature was added a solution of BBr$_3$ (0.3 mL of 2M, 0.6 mmol). The resulting mixture was stirred at 90° C. for 36 hours. It was cooled to 0° C., quenched by MeOH (5 mL) and neutralized with NaHCO$_3$ solution. It was concentrated to remove the dichloroethane and the residue was purified by preparative HPLC (YMC OD S-10 30×500 mm; 60% B; flow rate 49 mL/minute; UV 254 nm). Those fractions containing the desired compound were pooled, concentrated and lyophilized to afford the title compound (9.5 mg, 26%) as a solid, mp 112° C.

$^1$H NMR (CD$_3$OD) δ7.59–7.29 (m, 5H), 6.30 (s, 1H), 5.22 (s, 1H), 4.20 (m, 1H), 3.55 (m, 3H), 3.12 (m, 3H), 2.87 (s, 3H), 1.84 (m, 1H) ppm;

$^{13}$C NMR (CD$_3$OD) δ186.3, 169.4, 164.2, 162.5, 155.5, 153.5, 132.2, 128.8, 122.4, 107.3, 104.6, 101.6, 88.9, 68.3, 62.2, 57.3, 44.6, 37.8, 23.6 ppm; MS (ESI.) m/e 384 (M+H)$^+$.

Anal Calc'd for C$_{21}$H$_{21}$NO$_6$.0.70 H$_2$O.1.70 C$_2$HF$_3$O$_2$: C, 49.68; H, 4.12; N, 2.37; Found: C, 49.65; H, 4.13; N, 2.45.

EXAMPLE 8 cis-(−)-2-[(2-Chlorophenyl)thio]5,7-dihydroxy-8-(3-hydroxy-1-methyl-4piperidinyl)-4H-1-benzopyran-4-one

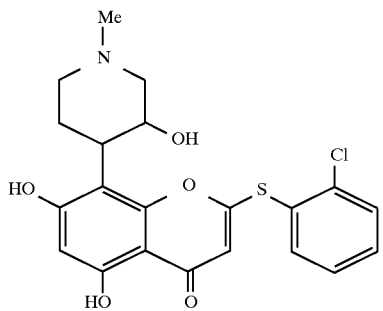

A. cis-(−)-2-(Ethylthio)-8-(3-hydroxy-1-methyl-4-piperidinyl)-5,7-dimethoxy-4H-1-benzopyran-4-one and cis-(+)-2-(Ethylthio)-8-(3-hydroxy-1-methyl-4-piperidinyl)-5,7-dimethoxy-4H-1-benzopyran-4one The title F compound of Example 1 (cis-(±)-2-(ethylthio)-8-(3-hydroxy-1-methyl-4-piperidinyl)-5,7-dimethoxy-4H-1-benzopyran-4-one: 1.3 g, 3.4 mmol) was dissolved in 60 mL of 30% ethanol in hexanes. It was divided into 5 portions. Each portion was resolved by the Chiralcel® OD column (50×500 mm, Daicel Chem, Industries, LTD; solvent system: 35% isopropanol in hexanes containing 0.1% triethylamine; Flow rate: 70 mL/minute; Detector: UV 280 nm). Every fraction was analyzed by an analytical Chiralcel® OD column (250×4.6 mm; flow rate: 2.0 mL/minute; UV: 254 nm; solvent system: 35% isopropanol in hexanes containing 0.1% triethylamine).

The fractions having a retention time of 5.86 minutes on an analytical column were combined and concentrated to afford cis-(−)-2-(ethylthio)-8-(3-hydroxy-1-methyl-4-piperidinyl)-5,7-dimethoxy-4H-1-benzopyran-4-one (544 mg, 84%) as a foam. [α]$_D$=−65.3° C. (MeOH, c 0.66);

The fractions having retention time of 8.76 minutes on an analytical column were combined and concentrated to afford cis-(+)-2-(ethylthio)-8-(3-hydroxy-1-methyl-4-piperidinyl)-5,7-dimethoxy-4H-1-benzopyran-4-one (550 mg, 85%) as a foam. [α]$_D$=+65.6° (MeOH, c 0.66).

B. cis-(−)-2-(Ethylthio)-5,7-dihydroxy-8-(3-hydroxy-1-methyl-4-piperidinyl)-4H-1-benzopyran-4-one To a solution of the title A compound (cis-(−)-2-(ethylthio)-8-(3-hydroxy-1-methyl-4-piperidinyl)-5,7-dimethoxy-4H-1-benzopyran-4-one: 180.5 mg, 0.476 mmol) in 1,2-dichloroethane (3 mL) was added a solution of BBr$_3$ (2.5 mL of 2M solution in 1,2-dichloroethane). The mixture was stirred at 90° C. or 3 hours and cooled to room temperature. It was quenched by MeOH (5 mL) and concentrated. The residue was re-dissolved in MeOH (10 mL) and neutralized by aqueous NaHCO$_3$ solution. The resulting solution was purified by HPLC (YMC OD S-10 30×500 mm; 45% B; flow rate 49 mL/minute; UV 254 nm). Those fractions containing the desired product were pooled, concentrated and lyophilized to afford the title compound (162 mg, 70%) as solid, mp 104° C. [α]$_D$=−19.0° (MeOH, c 0.52).

C. cis-(−)-2-[(2-Chlorophenyl)thio]-5,7-dihydroxy-8-(3-hydroxy-1-methyl-4-piperidinyl)-4H-1-benzopyran-4-one A mixture of the title B compound (150 mg, 0.31 mmol), 2-chlorothiophenol (356 mg, 3.1 mmol) and NaHCO$_3$ (500 mg, 5.95 mmol) in DMF (2 mL) was stirred at 90° C. for 4 hours. The mixture was cooled to room temperature, diluted with MeOH (10 mL) and neutralized with trifluoroacetic acid. The resulting mixture was purified directly by preparative HPLC (YMC OD S-10 30×500 mm; 60% B; flow rate 49 mL/minute; UV 254 nm). Those fractions containing the desired compound were pooled, concentrated and lyophilized to afford the title compound (80 mg, 43.6%) as a solid, mp 110° C. [α]$_D$=−7.3° (MeOH, c 0.56);

$^1$H NMR (CD$_3$OD) δ7.87–7.50 (m, 4H), 6.27 (s, 1H), 5.92 (s, 1H), 4.07 (m, 1H), 3.50–2.91 (m, 7H), 2.87 (s, 3H), 1.70 (m, 1H) ppm;

$^{13}$C NMR (CD$_3$OD) δ182.2, 168.7, 164.2, 162.2, 157.9, 140.3, 138.8, 133.9, 132.3, 129.9, 127.5,108.3, 106.8, 105.2, 101.4, 67.8, 61.8, 56.8, 44.3, 37.2, 23.1 ppm; MS (ESI.) (95120153) m/e 434 (M+H)$^+$; Anal Calc'd for C$_{21}$H$_{20}$NO$_5$ClS.0.5 H$_2$O.1.30 C$_2$HF$_3$O$_2$: C, 47.95; H, 3.80; N, 2.37; F, 12.53; Cl, 6.00; S, 5.42; Found: C, 47.87; H, 3.56; N, 2.32; F, 12.27; Cl, 6.67; S, 5.15.

Alternate Procedure For Preparation of Compounds of Example 8

A*. cis-(−)-2-(Ethylthio)-8-(3-hydroxy-1-methyl-4-piperidinyl)-5,7-dimethoxy-4H-1-benzopyran-4-one and cis-(+)-2-(Ethylthio)-8-(3-hydroxy-1-methyl-4-piperidinyl)-5,7-dimethoxy-4H-1-benzopyran-4-one The title F compound of Example 1 (cis-(+)-2-(ethylthio)-8-(3-hydroxy-1-methyl-4-piperidinyl)-5,7-dimethoxy-4H-1-benzopyran-4-one: 4.2 g, 11.1 mmol) was divided in two portions and resoluted by the Chiralcel® AD column (50× 500 mm, Daicel Chem, Industries, LTD; solvent system: 35% isopropanol in hexanes containing 0.1% triethylamine; Flow rate: 50 mL/minute; Detector: UV 280 nm). Every fraction was analyzed by an analytical chiralcel AD column (250×4.6 mm; flow rate: 2.0 mL/minute; UV: 254 nm; solvent system: 35% isopropanol in hexanes containing 0.1% triethylamine).

The fractions having R$_f$=22.0 minutes on an analytical column were combined and concentrated to afford cis-(−)-2-(ethylthio)-8-(3-hydroxy-1-methyl-4-piperidinyl)-5,7-dimethoxy-4H-1-benzopyran-4-one (1.67 g, 80%) as a foam.

The fractions having R$_f$=13.4 minutes on an analytical column were combined and concentrated to afford cis-(+)-2-(ethylthio)-8-(3-hydroxy-1-methyl-4-piperidinyl)-5,7-dimethoxy-4H-1-benzopyran-4-one (2.06 g, 98%) as a foam.

B*. cis-(−)-2-(Ethylsulfinyl)-8-(3-hydroxy-1-methyl-4-piperidinyl)-5,7-dimethoxy-4H-1-benzopyran-4-one trifluoroacetic acid salt To a solution of the title A* compound; cis-(−)-2-(ethylthio)-8-(3-hydroxy-1-methyl-4-piperidinyl)-5,7-dimethoxy-4H-1-benzopyran-4-one, (1.67 g, 4.41 mmol) in CH$_2$Cl$_2$ (18 mL) containing TFA (1.7 mL) at 0° C. was added m-chloroperbenzoic acid (1.42 g, 50–60% contents) as a solid with stirring. The mixture was stirred at 0° C. for 1 hour and it was quenched by adding dimethyl sulfide (1 mL). The mixture was stirred for 5 minutes and concentrated. To the residue was added ethyl ether (150 mL) and the mixture was stirred at room temperature for 30 minutes. The solid was collected and dried to obtain the title compound (2.15 g), which contained a small amount of over-oxidized sulfone compound. This crude material was used for the next reaction without any further purification.

C*. cis-(−)-2-[(2-Chlorophenyl)thio]-8-(3-hydroxy-1-methyl-4-piperidinyl)-5,7-dihydroxy-4H-1-benzopyran-4-one A mixture of potassium tert-butoxide (1.12 g, 10 mmol) and 2-chlorothiophenol (1.16 g, 8 mmol) in THF (10 mL) was stirred at room temperature under Argon atmosphere for 10 minutes. To this mixture at 0° C. was added a solution of the title B* compound (1.0 g, 1.96 mmol) in THF (10 mL). The resulting mixture was stirred at 0° C. for 1 hour and it was directly loaded onto a flash chromatography column (SiO$_2$) and was eluted with ethyl acetate (ca. 1 L) followed by EtOAc:MeOH:Et$_3$N (100:15:2) to afford the desired product. This material was dissolved in CH$_2$Cl$_2$ (100 mL), washed with aqueous NaHCO$_3$ solution, dried over Na$_2$SO$_4$ and concentrated to afford the title compound (830 mg, 92%) as a foam.

D*. cis-(−)-2-[(2-Chlorophenyl)thio]-5,7-dihydroxy-8-(3-hydroxy-1-methyl-4-piperidinyl)-4H-1-benzopyran-4-one To a solution of the title C* compound (0.81 g, 1.75 mmol) in 1,2-dichloroethane (15 mL) at room temperature was added a solution of BBr$_3$ (8.75 mL of 2M in 1,2-dichloroethane, 17.5 mmol). The mixture was stirred at 85°–90° C. for 3 hours and concentrated. The residue was cooled to −30° C. and methanol (30 mL) was added. It was stirred at room temperature with solid NaHCO$_3$ (2 g) for 20 minutes and acidified with TFA (1 mL). It was purified by preparative HPLC (YMC OD S-10 50×500 mm; 60% B; flow rate 84 mL/minute; UV 254 nm). Those fractions containing the desired compound were pooled, concentrated and lyophilized to afford the title compound (666 mg, 68%) as a solid, mp 223° C. (dec.).

Anal Calc'd for C$_{21}$H$_{20}$ClNO$_5$S.0.5 H$_2$O.1.00 C$_2$HF$_3$O$_2$: C, 49.60; H, 3.98; N, 2.51; F, 10.23; Cl, 6.37; S, 5.76; Found: C, 49.73; H, 3.95; N, 2.54; F, 10.17; Cl, 6.51; S, 5.94.

EXAMPLE 9 cis-(+)-2-[(2-Chlorophenyl)thio]-5,7-dihydroxy-8-(3-hydroxy-1-methyl-4-piperidinyl)-4-1-benzopyran-4-one

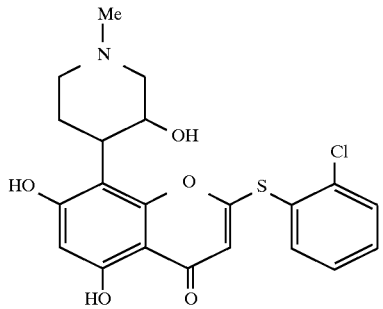

A. cis-(+)-2-(Ethylthio)-5,7-dihydroxy-8-(3-hydroxy-1-methyl-4-piperidinyl)-4H-1-benzopyran-4-one To a solution of the title A compound of Example 8 (cis-(+)-2-(ethylthio)-8-(3-hydroxy-1-methyl-4H-piperidinyl)-5,7-dimethoxy-4H-1-benzopyran-4-one: 180.5 mg, 0.476 mmol) in 1,2-dichloroethane (3 mL) was added a solution of BBr$_3$ (2.5 mL of 2M solution in 1,2-dichloroethane). The mixture was stirred at 90° C. or 3 hours and cooled to room temperature. It was quenched by MeOH (5 mL) and concentrated. The residue was re-dissolved in MeOH (10 mL) and neutralized by aqueous NaHCO$_3$ solution. The resulting solution was purified by HPLC (YMC OD S-10 30×500 mm; 45% B; flow rate 49 mL/minute; UV 254 nm). Those fractions containing the desired product were pooled, concentrated and lyophilized to afford the title compound (163 mg, 70%) as solid, mp 103° C. [α]$_D$=+19.1° (MeOH, c 0.70).

B. cis-(+)-2-[(2-Chlorophenyl)thio]-5,7-dihydroxy-8-(3-hydroxy-1-methyl-4-piperidinyl)-4H-1-benzopyran-4-one A mixture of the title A compound (150 mg, 0.31 mmol), 2-chlorothiophenol (356 mg, 3.1 mmol) and NaHCO$_3$ (500 mg, 5.95 mmol) in DMF (2 mL) was stirred at 90° C. for 4 hours. The mixture was cooled to room temperature, diluted with MeOH (10 mL) and neutralized with trifluoroacetic acid. The resulting mixture was purified directly by preparative HPLC (YMC OD S-10 30×500 mm; 60% B; flow rate 49 mL/minute; UV 254 nm). Those fractions containing the desired compound were pooled, concentrated and lyophilized to afford the title compound (75 mg, 40%) as a solid, mp 109° C. [α]$_D$=+7.6° C. (MeOH, c 0.59);

$^1$H NMR (CD$_3$OD) δ7.87–7.50 (m, 4H), 6.27 (s, 1H), 5.92 (s, 1H), 4.07 (m, 1H), 3.50–2.91 (m, 7H), 2.87 (s, 3H), 1.70 (m, 1H) ppm;

$^{13}$C NMR (CD$_3$OD) δ182.6, 169.1, 164.6, 162.7, 158.4, 140.7, 139.2, 134.3, 132.7, 130.3, 127.9, 108.7, 107.2, 105.6, 101.7, 68.2, 62.2, 57.2, 44.7, 37.7, 23.5 ppm; MS (ESI.) (95120155) m/e 434 (M+H)$^+$; Anal Calc'd for C$_{21}$H$_{20}$NO$_5$ClS.0.8 H$_2$O.1.4 C$_2$HF$_3$O$_2$: C, 47.02; H, 3.81; N, 2.30; F, 13.12; Cl, 5.83; S, 5.27; Found: C, 47.04; H, 3.58; N, 2.03; F, 12.96; Cl, 6.04; S, 5.21.

EXAMPLE 10 cis-(±)-2-(2-Chlorophenoxy)-5,7-dihydroxy-8-(3-hydroxy-1-methyl-4-piperidinyl)-4H-1-benzopyran-4-one

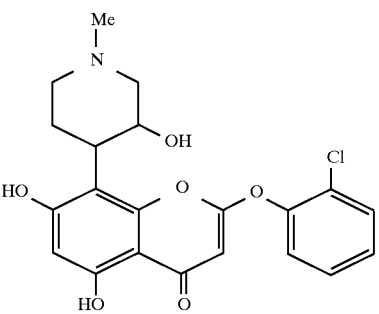

A. cis-(±)-2-(2-Chlorophenoxy)-8-(3-hydroxy-1-methyl-4-piperidinyl)-5,7-dimethoxy-4H-1-benzopyran-4-one A mixture of 2-chlorophenol (64 mg, 0.5 mmol) and NaH (20 mg, 60% in oil, 0.5 mmol) in THF (2 mL) was stirred at room temperature for 10 minutes and the title A compound of Example 7 (2-(ethylsulfinyl)-8-(3-hydroxy-1-methyl-4-piperidinyl)-5,7-dimethoxy-4H- 1-benzopyran-4-one: 95 mg, 0.24 mmol) was added as a solid. The resulting mixture was stirred for 2 hours and concentrated. The residue was taken up in CH$_2$Cl$_2$ (20 mL), washed with water (10 mL) and dried (Na$_2$SO$_4$). It was concentrated and purified by flash column chromatography (SiO$_2$, EtOAc:MeOH:Et$_3$N; 100:15:2) to afford the title compound (56 mg, 52%) as a solid, mp 206°–207° C.

B. cis-(±)-2-(2-Chlorophenoxy)-5,7-dihydroxy-8-(3-hydroxy-1-methyl-4-piperidinyl)-4H-1-benzopyran-4-one To a solution of the title A compound (47 mg, 0.105 mmol) in 1,2-dichloroethane (2 mL) at room temperature was added a solution of BBr$_3$ (0.5 mL of 2M solution, 1.0 mmol) in 1,2-dichloroethane. The resulting mixture was stirred at 75°–80° C. for 4 hours. It was cooled to 0° C., quenched by MeOH (5 mL) and neutralized with NaHCO$_3$ solution. It was concentrated to remove the dichloroethane and the residue was purified by preparative HPLC (YMC OD S-10 30×500 mm; 55% B; flow rate 49 mL/minute; UV 254 nm). Those fractions containing the desired compound were pooled, concentrated and lyophilized to afford the title compound (30.5 mg, 46%) as a solid, mp 122° C.

$^1$H NMR (CD$_3$OD) δ7.65 (m, 1H), 7.48 (m, 3H), 6.31 (s, 1H), 5.20 (s, 1H), 4.19 (m, 1H), 3.32 (m, 3H), 3.29 (m, 3H), 2.86 (s, 3H), 1.81 (m, 1H) ppm;

$^{13}$C NMR (CD$_3$OD) δ185.7, 167.7, 163.9, 162.1, 155.1, 148.5, 132.5, 130.4, 130.0, 127.6, 124.5, 106.9, 104.1, 101.3, 88.3, 67.8, 61.8, 56.8, 44.2, 37.5, 23.2 ppm; MS (ESI.) (#96010023) m/e 418 (M+H)$^+$;

Anal Calc'd for C$_{21}$H$_{20}$ClNO$_6$.0.80 H$_2$O.1.70 C$_2$HF$_3$O$_2$: C, 46.81; H, 3.75; N, 2.24; Found: C, 47.03; H, 3.51; N, 2.28.

EXAMPLE 11 cis-(±)-5,7-Dihydroxy-8-(3-hydroxy-1-methyl-4-piperidinyl)-2-[(phenylmethyl)thio]4H-1-benzopyran-4-one, trifluoroacetate

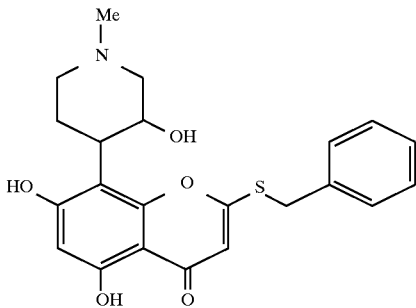

A mixture of the title compound of Example 1 (cis-(±)-2-(ethylthio)-5,7-dihydroxy-8-(3-hydroxy-1-methyl-4-piperidinyl)-4H-1-benzopyran-4-one: 70 mg, 0.15 mmol), benzyl mercaptan (124 mg, 1 mmol) and Cs$_2$CO$_3$ (100 mg) in DMF (1.0 mL) was stirred at 90° C. for 10 hours. The mixture was cooled to room temperature and diluted with water (1 mL) and methanol (4 mL). The resulting solution was acidified with TFA and purified directly by preparative HPLC (YMC OD S-10 30×500 mm; 50% B; flow rate 49 mL/minute; UV 254 nm). Those fractions containing the desired compound were pooled, concentrated and lyophilized to afford the title compound (22 mg, 26%) as a solid, mp 105° C.

$^1$H NMR (CD$_3$OD) δ7.45–7.30 (m, 5H), 6.27 (s, 1H), 6.21 (s, 1H), 4.42 (m, 2H), 4.19 (m, 1H), 3.57 (m, 3H), 3.24 (m, 3H), 2.86 (s, 3H), 1.85 (m, 1H) ppm;

$^{13}$C NMR (CD$_3$OD) δ182.1, 170.3, 164.0, 162.3, 158.2, 136.7, 130.0, 129.1, 108.1, 106.7, 105.2, 100.9, 67.9, 61.8, 56.7, 44.2, 37.4, 36.7, 23.3 ppm; MS (ESI.) m/e 414 (M+H)$^+$;

Anal Calc'd for C$_{22}$H$_{23}$NO$_5$S.0.60 H$_2$O.1.30 C$_2$HF$_3$O$_2$: C, 51.61; H, 4.49; N, 2.41; Found: C, 51.49; H, 4.20; N, 2.41.

EXAMPLE 12 cis-(±)-5,7-Dihydroxy-8-(3-hydroxy-1-methyl-4-piperidinyl)-2-[(4-methoxyphenyl)thio]4H-1-benzopyran-4-one, trifluoroacetate

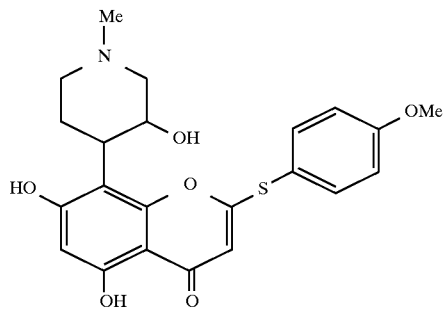

A mixture of the title compound of Example 1 (cis-(±)-2-(ethylthio)-5,7-dihydroxy-8-(3-hydroxy-1-methyl-4-piperidinyl)-4H-1-benzopyran-4-one: 100 mg, 0.2 mmol), 4-methoxy-thiophenol (148 mg, 1 mmol) and NaHCO$_3$ (200 mg) in DMF (1.0 mL) was stirred at 85° C. for 3 hours. The mixture was cooled to room temperature and diluted with water (5 mL). It was extracted with CH$_2$Cl$_2$ (3×10 mL). The CH$_2$Cl$_2$ extract was dried over Na$_2$SO$_4$ and concentrated. The residue was dissolved in methanol (1 mL) and loaded onto an ion-exchange resin cartridge (Varian® Mega Bond Elut SCX, 3 grams/6 mL), which was pre-conditioned with methanol. The cartridge was first eluted with methanol (10 mL) and then eluted with 2% ammonia in methanol to collect the basic fractions. The basic fractions were combined and concentrated. The residue was purified by automated preparative HPLC (YMC-pack, ODSA, S-5 30×250 mm; solvent system: gradient from 20% to 100% B in 30 minutes; flow rate 25 mL/minute; UV 254 nm). Those containing the desired compound were pooled, concentrated and lyophilized to afford the title compound (15 mg, 13%) as a solid, mp 99° C.

$^1$H NMR (CD$_3$OD) δ7.65 (d, J=8.7 Hz, 2H), 7.15 (d, J=8.7 Hz, 2H), 6.25 (s, 1H), 5.76 (s, 1H), 4.10 (m, 1H), 3.90 (s, 3H), 3.55–3.46 (m, 3H), 3.12–2.95 (m, 3H), 2.89 (s, 3H), 1.74 (m, 1H) ppm;

$^{13}$C NMR (CD$_3$OD) δ182.1, 172.7, 164.0, 163.4, 162.2, 157.8, 138.9, 117.6, 117.1, 106.4, 105.1, 101.2, 67.9, 61.7, 56.8, 56.3, 44.2, 37.1, 23.1 ppm; MS (ESI.) m/e 430 (M+H)$^+$.

EXAMPLE 13 cis-(±)-5,7-Dihydroxy-8-(3-hydroxy-1-methyl-4-piperidinyl)-2-[[(4-methoxyphenyl)methyl]thio]-4H-1-benzopyran-4-one, trifluoroacetate

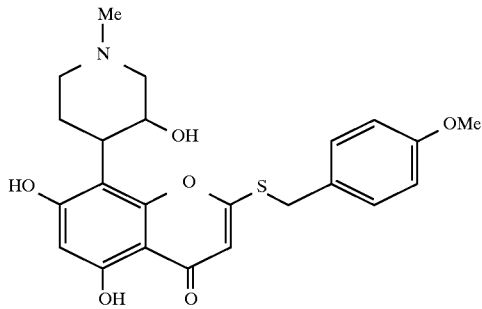

A mixture of the title compound of Example 1 (cis-(±)-2-(ethylthio)-5,7-dihydroxy-8-(3-hydroxy-1-methyl-4-piperidinyl)-4H-1-benzopyran-4-one: 100 mg, 0.2 mmol), 4-methoxybenzyl mercaptan (160 mg, 1 mmol) and $NaHCO_3$ (200 mg) in DMF (1.0 mL) was stirred at 85° C. for 2 hours. The mixture was cooled to room temperature and directly loaded onto an ion-exchange resin cartridge (Varian® Mega Bond Elut SCX, 3 grams/6 mL), which was pre-conditioned with methanol. The cartridge was first eluted with methanol (10 mL) and then eluted with 2% ammonia in methanol to collect the basic fractions. The basic fractions were combined and concentrated. The residue was purified by automated preparative HPLC (YMC-pack, ODSA, S-5 30×250 mm; solvent system: gradient from 20% to 100% B in 30 minutes; flow rate 25 mL/minute; UV 254 nm). Those fractions containing the desired compound were pooled, concentrated and lyophilized to afford the title compound (46 mg, 40%) as a solid, mp 103° C.

$^1H$ NMR ($CD_3OD$) δ7.34 (d, J=8.2 Hz, 2H), 6.90 (d, J=8.2 Hz, 2H), 6.27 (s, 1H), 6.20 (s, 1H), 4.37 (m, 2H), 4.20 (m, 1H), 3.78 (s, 3H), 3.57 (m, 3H), 3.15 (m, 3H), 2.86 (s, 3H), 1.85 (m, 1H) ppm;

$^{13}C$ NMR ($CD_3OD$) δ182.1, 170.9, 164.0, 162.2, 161.0, 158.2, 131.2, 128.2, 115.3, 107.9, 106.7, 105.2, 100.9, 67.9, 61.8, 56.7, 55.8, 44.2, 37.4, 36.4, 23.3 ppm; MS (ESI.) m/e 444 $(M+H)^+$.

EXAMPLE 14 cis-(±)-N-[2-[[5,7-Dihydroxy-8-(3-hydroxy-1-methyl-4-piperidinyl)-4-oxo4H-1-benzopyran-2-yl]thio]ethyl]acetamide, trifluoroacetate

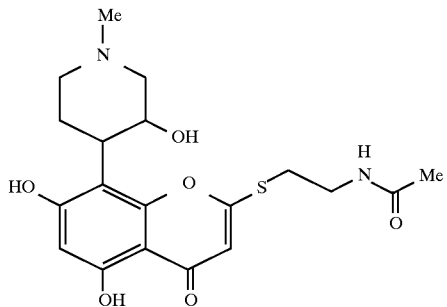

A mixture of the title compound of Example 1 (cis-(±)-2-(ethylthio)-5,7-dihydroxy-8-(3-hydroxy-1-methyl-4-piperidinyl)-4H-1-benzopyran-4-one: 100 mg, 0.2 mmol), N-acetylcysteamine (119 mg, 1 mmol) and $NaHCO_3$ (200 mg) in DMF (1.0 mL) was stirred at 85° C. for 3 hours. The mixture was cooled to room temperature and directly loaded onto an ion-exchange resin cartridge (Varian® Mega Bond Elut SCX, 3 grams/6 mL), which was pre-conditioned with methanol. The cartridge was first eluted with methanol (10 mL) and then eluted with 2% ammonia in methanol to collect the basic fractions. The basic fractions were combined and concentrated. The residue was purified by automated preparative HPLC (YMC-pack, ODSA, S-5 30×250 mm; solvent system: gradient from 20% to 100% B in 30 minutes; flow rate 25 mL/minute; UV 254 nm). Those fractions containing the desired compound were pooled, concentrated and lyophilized to afford the title compound (67 mg, 62%) as a solid, mp 86° C.

$^1H$ NMR ($CD_3OD$) δ6.30 (s, 1H), 6.29 (s, 1H), 4.27 (m, 1H), 3.62–3.23 (m, 6H), 2.92 (s, 3H), 1.89 (s, 3H), 1.88 (m, 1H) ppm;

$^{13}C$ NMR ($CD_3OD$) δ182.2, 173.7, 169.7, 164.1, 162.3, 158.2, 108.5, 106.9, 105.3, 101.1, 68.0, 61.7, 56.7, 44.2, 40.0, 37.3, 31.5, 23.3, 22.5 ppm; MS (ESI.) m/e 409 $(M+H)^+$.

EXAMPLE 15 cis-(±)-5,7-Dihydroxy-2-[(2-hydroxyethyl)thio]-8-(3-hydroxy-1-methyl-4-piperidinyl)-4H-1-benzopyran-4-one, trifluoroacetate

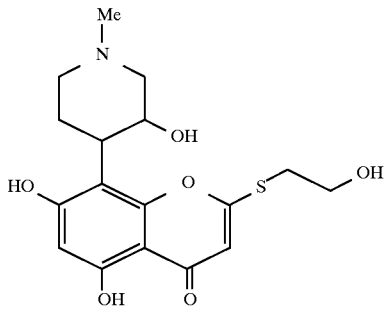

A mixture of the title compound of Example 1 (cis-(±)-2-(ethylthio)-5,7-dihydroxy-8-(3-hydroxy-1-methyl-4-piperidinyl)-4H-1-benzopyran-4-one: 100 mg, 0.2 mmol), 2-mercaptoethanol (78 mg, 1 mmol) and $NaHCO_3$(200 mg) in DMF (1.0 mL) was stirred at 85° C. for 3 hours. The mixture was cooled to room temperature and directly loaded onto an ion-exchange resin cartridge (Varian® Mega Bond Elut SCX, 3 grams/6 mL), which was pre-conditioned with methanol. The cartridge was first eluted with methanol (10 mL) and then eluted with 2% ammonia in methanol to collect the basic fractions. The basic fractions were combined and concentrated. The residue was purified by automated preparative HPLC (YMC-pack, ODSA, S-5 30×250 mm; solvent system: gradient from 20% to 100% B in 30 minutes; flow rate 25 mL/minute; UV 254 nm). Those fractions containing the desired compound were pooled, concentrated and lyophilized to afford the title compound (14.8 mg, 15%) as a solid, mp 78° C.

$^1H$ NMR ($CD_3OD$) δ6.28 (s, 1H), 6.23 (s, 1H), 4.26 (m, 1H), 3.84 (t, J=7.0 Hz, 2H), 3.67–3.20 (m, 8H), 2.90 (s, 3H), 1.88 (m, 1H) ppm; MS (ESI.) m/e 368 $(M+H)^+$.

EXAMPLE 16 cis-(−)-2-(2-Chlorophenoxy)-5,7-dihydroxy-8-(3-hydroxy-1-methyl-4-piperidinyl)-4H-1-benzopyran-4-one

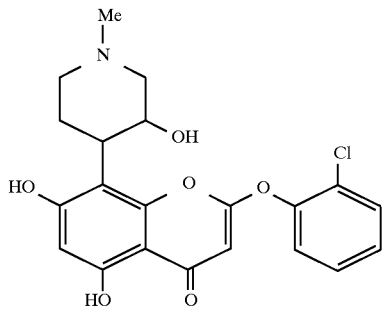

A. cis-(−)-2-(2-Chlorophenoxy)-8-(3-hydroxy-1-methyl-4-piperidinyl)-5,7-dimethoxy-4H-1-benzopyran-4-one A mixture of 2-chlorophenol (1.0 mL, 9.65 mmol) and potassium t-butoxide (1.20 g, 10.69 mmol) in anhydrous THF (12 mL) was stirred for 10 minutes at room temperature. It was cooled in an ice bath and a solid of the sulfoxide of Example 8B*; cis-(−)-2-(ethylsulfinyl)-8-(3-hydroxy-1-methyl-4-piperidinyl)-5,7-dimethoxy-4H-1-benzopyran-4-one (1.15 g, 2.26 mmol) was added. The reaction mixture was stirred at 0°–5° C. for 1.5 hours. After adding acetic acid (0.25 mL) to the mixture it was directly loaded onto a silica gel column and eluted by ethylacetate followed by EtOAc:MeOH:Et3N (100:20:2) to obtain a product containing trifluoroacetic acid and triethylamine. This material was mixed with chloroform (60 mL) and aq. NaHCO$_3$ (10 mL) solution, the organic layer was taken, dried over magnesium sulfate and concentrated to obtain 760 mg of the title compound as a floppy glassy material in 75.6% yield.

B. cis-(−)-2-(2-Chlorophenoxy)-5,7-dihydroxy-8-(3-hydroxy-1-methyl-4-piperidinyl)-4H-1-benzopyran-4-one To a solution of the title A compound (760 mg, 1.70 mmol) in 1,2-dichloroethane (20 mL) at room temperature was added a solution of BBr$_3$ (8.5 mL of 2M in 1,2-dichloroethane, 17.0 mmol). The mixture was stirred at 80° C. for 5 hours and concentrated. The residue was cooled to −30° C. and methanol (10 mL) was added to the mixture. It was stirred at room temperature with solid NaHCO$_3$ (1.5 g) for 10 minutes and acidified with TFA (0.5 mL). It was purified by preparative HPLC (YMC OD S-10 50×500 mm; 55% B; flow rate 84 mL/minute; UV 254 nm). Those fractions containing the desired compound were pooled, concentrated and lyophilized to afford the title compound (505 mg, 53%) as a solid, mp 105° C. (softened). [α]$_D$=−22.4° C. (MeOH, c 0.7);

$^1$H NMR (CD$_3$OD) δ7.65 (d, J=8.2 Hz, 1H), 7.48 (m, 3H), 6.30 (s, 1H), 5.20 (s, 1H), 4.20 (m, 1H), 3.51 (m, 3H), 3.18 (m, 3H), 2.87 (s, 3H), 1.80 (m, 1H) ppm;

$^{13}$C NMR (CD$_3$OD) δ186.5, 168.5, 164.8, 162.8, 155.8, 149.2, 133.3, 131.2, 130.8, 128.4, 125.3, 107.8, 104.8, 102.1, 89.1, 68.6, 62.5, 57.6, 45.0, 38.2, 24.0 ppm. MS (ESI.) (96040448 m/e 418 (M+H)$^+$;

Anal Calc'd for C$_{21}$H$_{20}$ClNO$_6$.0.5 H$_2$O.1.15 C$_2$HF$_3$O$_2$: C, 50.16; H, 4.00; N, 2.51; F, 11.75; Cl, 6.35; Found: C, 49.92; H, 3.78; N, 2.48; F, 11.58; Cl, 6.65.

Using the procedures described herein or by modification of the procedures described herein as known to one of ordinary skill in the art, the following additional compounds have been prepared:

TABLE 1

| Example # | Molecular Structure | Molecular Formula | Mol. Weight Confirmed by Mass Spec. |
|---|---|---|---|
| 17 | 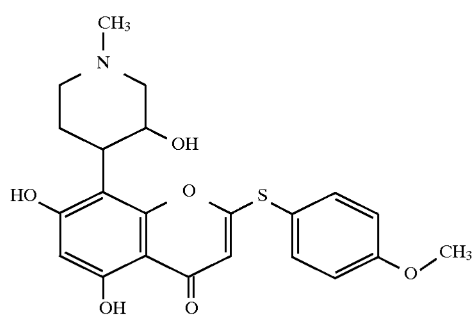 | C22H23NO6S | 429.49571 |
| 18 | 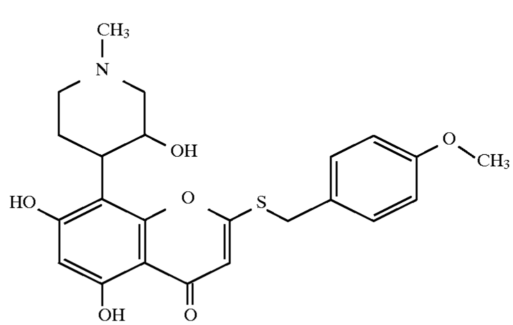 | C23H25NO6S | 443.5228 |

TABLE 1-continued
| Example # | Molecular Structure | Molecular Formula | Mol. Weight Confirmed by Mass Spec. |
|---|---|---|---|
| 19 | 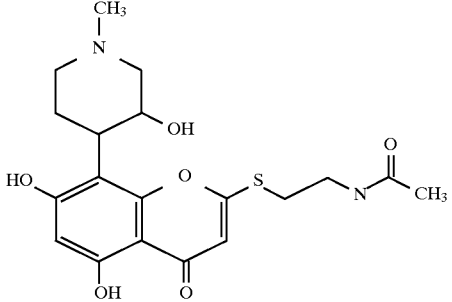 | C19H24N2O6S | 408.47693 |
| 20 | 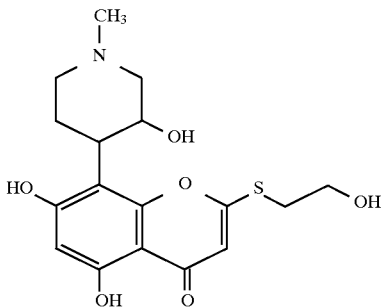 | C17H21NO6S | 367.42402 |
| 21 | 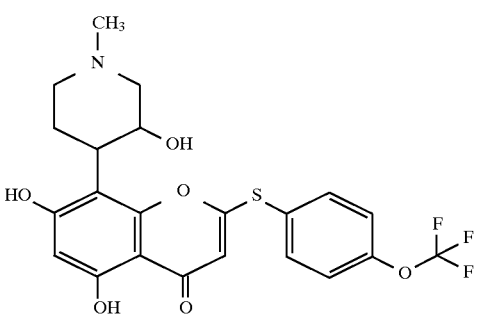 | C22H20F3NO6S | 483.467 |
| 22 | 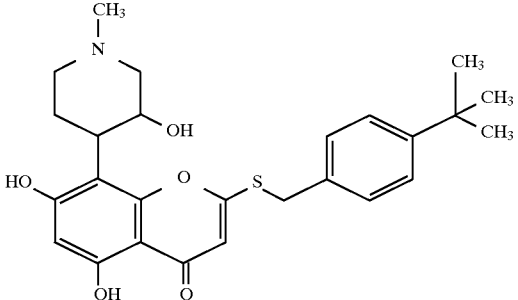 | C26H31NO5S | 469.60467 |

TABLE 1-continued

| Example # | Molecular Structure | Molecular Formula | Mol. Weight Confirmed by Mass Spec. |
|---|---|---|---|
| 23 | 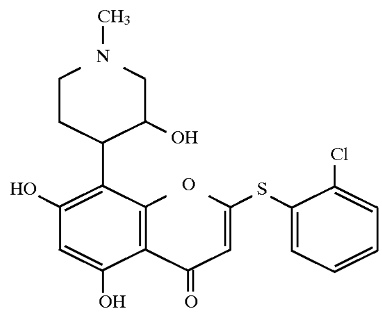 | C21H20ClNO5S | 433.91425 |
| 24 | 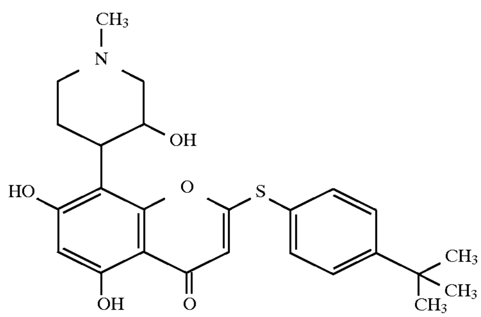 | C25H29NO5S | 455.57758 |
| 25 | 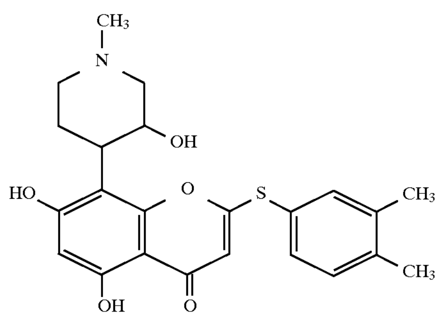 | C23H25NO5S | 427.5234 |
| 26 | 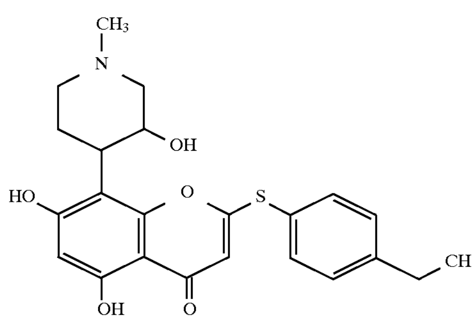 | C23H25NO5S | 427.5234 |

TABLE 1-continued

| Example # | Molecular Structure | Molecular Formula | Mol. Weight Confirmed by Mass Spec. |
|---|---|---|---|
| 27 | 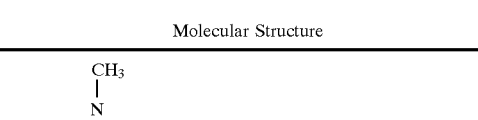 | C23H24N2O6S | 456.52153 |

Using the procedures described herein or by modification of the procedures described herein as known by one of ordinary skill in the art, the following additional compounds may also be prepared:

TABLE 2

| Example # | $R^1$ | $R^2$ | X | $R^3$ | $R^4$ | $R^5$ | $R^6$ |
|---|---|---|---|---|---|---|---|
| 28 | CH3 | CH | O | 2-Cl-4-F-Ph | H | 5-OH, 7-OH | H |
| 29 | CH3 | CH | S | 2-Cl-4-F-Ph | H | 5-OH, 7-OH | H |
| 30 | CH3 | NH2 | O | 2-ClPh | H | 5-0H, 7-OH | H |
| 31 | CH3 | NH2 | S | 2-ClPh | H | 5-OH, 7-OCOCH3 | H |
| 32 | CH2Ph | OH | 0 | 2-ClPh | COOCH3 | 5-OH, 7-OH | H |
| 33 | CH2Ph | OH | S | 1-naphthyl | H | 5-0H, 7-OH | H |
| 34 | CH3 | OH | O | 2-ClPh | H | 5-OH, 7-OH | CH3 |
| 35 | CH3 | OH | S | 2-ClPh | H | 5-OH, 7-OH | CH3 |
| 36 | CH(CH3)2 | OCH | O | 2-ClPh | H | 5-OH, 7-OH | CH2CH2OH |
| 37 | CH3 | OH | S | 2-ClPh | H | 5-NH2, 7-OH | CH2CH2OH |
| 38 | CH3 | OH | O | 2-Cl-4-CF3-Ph | H | 5-OH, 7-OH | H |
| 39 | CH3 | OH | S | 2-Cl-4-CF3-Ph | H | 5-OH, 7-OH | H |
| 40 | CH3 | OH | O | CH2tButyl | H | 5-CN | CH |
| 41 | CH3 | NH2 | S | CH2tButyl | H | 5-OH, 7-OH | H |
| 42 | CH3 | OH | O | 2-ClPh | CH3 | 5-OH, 7-OH | H |
| 43 | CH2CH2Ph | OH | S | 2-ClPh | CH3 | 5-OH, 7-OH | H |
| 44 | CH3 | NHCOCH3 | O | 2-ClPh | CH2CH2OH | 5-NO2, 7-OH | NH2 |
| 45 | CH3 | OH | S | 2-ClPh | CH2CH2OH | 5-OH, 7-OH | H |
| 46 | CH3 | OH | O | Cyclohexyl | H | 7-NH2 | H |
| 47 | CH3 | OH | S | Cyclohexyl | H | 5-OH, 7-OH | H |
| 48 | cyclohexyl | OH | O | 4-Pyridyl | H | 5-OH, 7-OH | H |
| 49 | CH3 | OH | S | 4-Pyridyl | H | 5-OH, 7-OH | H |
| 50 | CH3 | N(CH3)2 | O | 2-Cl-4-Pyridyl | H | 5-OH, 7-OH | H |
| 51 | CH3 | OH | S | 2-Cl-4-Pyridyl | H | 5-OH, 7-OH | H |
| 52 | CH3 | OH | O | 2-ClPh | H | 5-OH, 7-CH2OH | H |
| 53 | CH3 | OH | S | B-quinolinyl | H | 5-OH, 7-CH2OH | H |
| 54 | CH3 | OH | O | 2-ClPh | NHCH2Ph | 5-CH2OH, 7-OH | H |
| 55 | CH3 | OH | S | 2-ClPh | H | 5-CH2OH, 7-OH | H |
| 56 | CH(CH3)2 | OH | O | CH2CH2OH | H | 5-CN, 7-N02 | CH3 |
| 57 | 2,4-(NO2)Ph | NH(OH2Ph) | S | CH2CH2Ph | CH3 | 5-CHO | CH2CH3 |
| 58 | cyclohexyl | OH | O | 1-naphthyl | CH2CH3 | 7-CHO | CH |
| 59 | CH2CH2Ph | OH | S | CH2CH2OH | H | 7-OCON(CH3)2 | OCH3 |
| 60 | (CH2)3Ph | NHCOCH3 | O | C(CH3)3 | H | 5-OH, 7-OH | COOCH3 |
| 61 | (CH2)3CH3 | OH | S | C(CH3)3 | CH2Ph | 7-COOH | H |

What is claimed is:

1. A compound of the formula

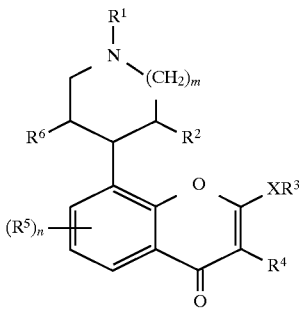

or pharmaceutically acceptable salts thereof wherein:

X is oxygen or sulfur;

$R^1$ is hydrogen, alkyl, aryl, arylalkyl, cycloalkyl, $-(CH_2)_q-NR^7R^8$, alkylcarbonyl, arylcarbonyl, arylalkylcarbonyl, alkyloxycarbonyl, arylalkyloxycarbonyl or aryloxycarbonyl;

$R^2$ is hydrogen, alkyl, arylalkyl, aryl, cycloalkyl, hydroxy, alkoxy, arylalkoxy, aryloxy, alkylcarbonyloxy, arylalkylcarbonyloxy, arylcarbonyloxy, carboxy, alkyloxycarbonyl, arylalkoxycarbonyl, aryloxycarbonyl, amino, $-NR^7R^8$, thiol, alkylthio, arylalkylthio or arylthio;

$R^3$ is alkyl, cycloalkyl, aryl or substituted aryl, arylalkyl, -5 or 6 membered heterocycle or -5 or 6 membered heterocycloalkyl;

$R^4$ is hydrogen, alkyl, aryl, arylalkyl, nitro, amino, $-(CH_2)_p-NR^7R^8$, halogen, hydroxy, alkoxy, carboxy, -5 or 6 membered heterocycle or alkyloxycarbonyl;

$R^5$ is hydrogen, alkyl, arylalkyl, aryl, cycloalkyl, hydroxy, alkoxy, arylalkoxy, aryloxy, alkylcarbonyloxy, arylalkylcarbonyloxy, arylcarbonyloxy, carboxy, alkyloxycarbonyl, arylalkoxycarbonyl, cyano, nitro, $-NR^7R^8$, halogen, alkylhalo, $-CHO$, alkyl$S(O)_m-$ or $-OC(O)NR^7R^8$;

$R^6$ is hydrogen, alkyl, arylalkyl, aryl, cycloalkyl, hydroxy, alkoxy, arylalkoxy, aryloxy, alkylcarbonyloxy, arylalkylcarbonyloxy, arylcarbonyloxy, carboxy, alkyloxycarbonyl, arylalkoxycarbonyl, aryloxycarbonyl, amino, $-NR^7R^8$, thiol, alkylthio, arylalkylthio or arylthio;

$R^7$ and $R^8$ are independently hydrogen, alkyl, aryl, arylalkyl, cycloalkyl, heterocycle or alkylcarbonyl; or $R^7$ and $R^8$ together with the nitrogen atom to which they are bonded can form a -5 or 6 membered heterocycle;

m is an integer of 0 to 2;

n is an integer of 0 to 3;

p is an integer of 1 to 3; and q is an integer of 2 to 5.

2. The compounds as recited in claim 1 wherein
$R^1$ is alkyl;
$R^2$ is hydroxy;
$R^3$ is alkyl, aryl, -5 or 6 member heterocycle or arylalkyl;
$R^4$ is hydrogen;
$R^5$ is hydroxy or alkoxy;
$R^6$ is hydrogen;
m is the integer 1; and
n is the integer 2.

3. The compounds as recited in claim 1 wherein
$R^1$ is alkyl;
$R^2$ is hydroxy;
$R^3$ is alkyl;
$R^4$ is hydrogen;
$R^5$ is hydroxy or alkoxy;
$R^6$ is hydrogen;
m is the integer 1; and
n is the integer 2.

4. The compounds as recited in claim 1 wherein
$R^1$ is alkyl;
$R^2$ is hydroxy;
$R^3$ is aryl;
$R^4$ is hydrogen;
$R^5$ is hydroxy or alkoxy;
$R^6$ is hydrogen;
m is the integer 1; and
n is the integer 2.

5. The compounds as recited in claim 1 wherein
$R^1$ is alkyl;
$R^2$ is hydroxy;
$R^3$ is haloaryl;
$R^4$ is hydrogen;
$R^5$ is hydroxy or alkoxy;
$R^6$ is hydrogen;
m is the integer 1; and
n is the integer 2.

6. The compounds as recited in claim 1 wherein
$R^1$ is alkyl;
$R^2$ is hydroxy;
$R^3$ is arylalkyl;
$R^4$ is hydrogen;
$R^5$ is hydroxy or alkoxy;
$R^6$ is hydrogen;
m is the integer 1; and
n is the integer 2.

7. The compounds as recited in claim 1 wherein
$R^1$ is alkyl;
$R^2$ is hydroxy;
$R^3$ is -5 or 6 membered heterocycle;
$R^4$ is hydrogen;
$R^5$ is hydroxy or alkoxy;
$R^6$ is hydrogen;
m is the integer 1; and
n is the integer 2.

8. The compounds as recited in claim 1 wherein
$R^1$ is alkyl;
$R^2$ is hydroxy;
$R^3$ is aryl;
$R^4$ is hydrogen;
$R^5$ is hydroxy;
$R^6$ is hydrogen;
m is the integer 1; and
n is the integer 2.

9. A compound selected from the group consisting of
cis-(±)-2-(ethylthio)-5,7-dihydroxy-8-(3-hydroxy-1-methyl-4-piperidinyl)-4H-1-benzopyran-4-one;
cis-(±)-5,7-dihydroxy-8-(3-hydroxy-1-methyl-4-piperidinyl)-2-(phenylthio)-4H-1-benzopyran-4-one;

cis-(±)-2-(butylthio)-5,7-dihydroxy-8-(3-hydroxy-1-methyl-4-piperidinyl)-4H-1-benzopyran-4-one;

cis-(±)-2-(ethylthio)-5-hydroxy-8-(3-hydroxy-1-methyl-4-piperidinyl)-7-methoxy-4H-1-benzopyran-4-one;

cis-(±)-3-[[5,7-dihydroxy-8-(3-hydroxy-1-methyl-4-piperidinyl)-4-oxo-4H-1-benzopyran-2-yl]thio]propanoic acid, methyl ester;

cis-(±)-2-[(2-chlorophenyl)thio]-5,7-dihydroxy-8-(3-hydroxy-1-methyl-4-piperidinyl)-4H-1-benzopyran-4-one;

cis-(±)-5,7-dihydroxy-8-(3-hydroxy-1-methyl-4-piperidinyl)-2-phenoxy-4H-1-benzopyran-4-one;

cis-(−)-2-[(2-chlorophenyl)thio]-5,7-dihydroxy-8-(3-hydroxy-1-methyl-4-piperidinyl)-4H-1-benzopyran-4-one;

cis-(+)-2-[(2-chlorophenyl)thio]-5,7-dihydroxy-8-(3-hydroxy-1-methyl-4-piperidinyl)-4H-1-benzopyran-4-one;

cis-(±)-2-(2-chlorophenoxy)-5,7-dihydroxy-8-(3-hydroxy-1-methyl-4-piperidinyl)-4H-1-benzopyran-4-one;

cis-(−)-2-(2-chlorophenoxy)-5,7-dihydroxy-8-(3-hydroxy-1-methyl-4-piperidinyl)-4H-1-benzopyran-4-one;

cis-(±)-5,7-dihydroxy-8-(3-hydroxy-1-methyl-4-piperidinyl)-2-[(phenylmethyl)thio]-4H-1-benzopyran-4-one, trifluoroacetate;

cis-(±)-5,7-dihydroxy-8-(3-hydroxy-1-methyl-4-piperidinyl)-2-[(4-methoxyphenyl)-thio]-4H-1-benzopyran-4-one, trifluoroacetate;

cis-(±)-5,7-dihydroxy-8-(3-hydroxy-1-methyl-4-piperidinyl)-2-[[(4-methoxyphenyl)methyl]-thio]-4H-1-benzopyran-4-one, trifluoroacetate;

cis-(±)-N-[2-[[5,7-dihydroxy-8-(3-hydroxy-1-methyl-4-piperidinyl)-4-oxo-4H-1-benzopyran-2-yl]thio]ethyl]acetamide, trifluoroacetate;

cis-(±)-5,7-dihydroxy-2-[(2-hydroxyethyl)thio]-8-(3-hydroxy-1-methyl-4-piperidinyl)-4H-1-benzopyran-4-one, trifluoroacetate; or a pharmaceutically acceptable salt thereof.

10. A method of inhibiting protein kinases which comprises administering to a mammalian specie in need thereof an effective protein kinase inhibiting amount of a compound of claim 1.

11. A method of inhibiting cyclin dependent kinases which comprises administering to a mammalian specie in need thereof an effective cyclin dependent kinase inhibiting amount of a compound of claim 1.

12. A method of inhibiting cdc2 (cdk1) which comprises administering to a mammalian specie in need thereof an effective cdc2 inhibiting amount of a compound of claim 1.

13. A method of inhibiting cdk2 which comprises administering to a mammalian specie in need thereof an effective cdk2 inhibiting amount of a compound of claim 1.

14. A method of inhibiting cdk3 which comprises administering to a mammalian specie in need thereof an effective cdk3 inhibiting amount of a compound of claim 1.

15. A method of inhibiting cdk4 which comprises administering to a mammalian specie in need thereof an effective cdk4 inhibiting amount of a compound of claim 1.

16. A method of inhibiting cdk5 which comprises administering to a mammalian specie in need thereof an effective cdk5 inhibiting amount of a compound of claim 1.

17. A method of inhibiting cdk6 which comprises administering to a mammalian specie in need thereof an effective cdk6 inhibiting amount of a compound of claim 1.

18. A method of inhibiting cdk7 which comprises administering to a mammalian specie in need thereof an effective cdk7 inhibiting amount of a compound of claim 1.

19. A method of inhibiting cdk8 which comprises administering to a mammalian specie in need thereof an effective cdk8 inhibiting amount of a compound of claim 1.

* * * * *